(12) United States Patent
Wagner et al.

(10) Patent No.: US 11,666,657 B2
(45) Date of Patent: Jun. 6, 2023

(54) PROTEIN-DRUG CONJUGATES AND THEIR USE IN THE TREATMENT OF CANCERS

(71) Applicants: UNIVERSITE DE STRASBOURG, Strasbourg (FR); CENTRE NATIONAL DE LA RECHERCHE SCIENTIFIQUE, Paris (FR)

(72) Inventors: Alain Wagner, Strasbourg (FR); Sergii Kolodych, Strasbourg (FR); Oleksandr Koniev, Strasbourg (FR)

(73) Assignees: UNIVERSITE DE STRASBOURG, Strasbourg (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 638 days.

(21) Appl. No.: 16/614,041

(22) PCT Filed: May 15, 2018

(86) PCT No.: PCT/EP2018/062546
§ 371 (c)(1),
(2) Date: Nov. 15, 2019

(87) PCT Pub. No.: WO2018/210824
PCT Pub. Date: Nov. 22, 2018

(65) Prior Publication Data
US 2020/0069815 A1    Mar. 5, 2020

(30) Foreign Application Priority Data

May 16, 2017 (EP) .................................. 17305563

(51) Int. Cl.
| | | |
|---|---|---|
| *A61K 47/68* | (2017.01) | |
| *A61K 47/64* | (2017.01) | |
| *A61K 47/65* | (2017.01) | |
| *A61P 35/00* | (2006.01) | |
| *A61K 38/07* | (2006.01) | |
| *C07K 16/28* | (2006.01) | |
| *C07K 16/32* | (2006.01) | |

(52) U.S. Cl.
CPC .......... *A61K 47/6803* (2017.08); *A61K 38/07* (2013.01); *A61K 47/643* (2017.08); *A61K 47/65* (2017.08); *A61K 47/6849* (2017.08); *A61K 47/6855* (2017.08); *A61P 35/00* (2018.01); *C07K 16/2887* (2013.01); *C07K 16/32* (2013.01)

(58) Field of Classification Search
None
See application file for complete search history.

(56) References Cited

U.S. PATENT DOCUMENTS

| | | | | |
|---|---|---|---|---|
| 7,723,485 | B2 * | 5/2010 | Junutula ............ | A61K 51/1027 435/7.1 |
| 2008/0311134 | A1 | 12/2008 | Junutula et al. | |

FOREIGN PATENT DOCUMENTS

| | | |
|---|---|---|
| EP | 2 641 618 | 9/2013 |
| EP | 3 130 356 | 2/2017 |
| WO | 2005/081711 | 9/2005 |
| WO | 2007/011968 | 1/2007 |
| WO | 2015/001117 | 1/2015 |
| WO | 2015/118497 | 8/2015 |
| WO | 2015/138615 | 9/2015 |

OTHER PUBLICATIONS

Lloyd et al., Protein Engineering, Design & Selection 22:159-168 (Year: 2009).*
Edwards et al., J Mol Biol. 334(1): 103-118 (Year: 2003).*
Piche-Nicholas et al., MABS 10(1): 81-94 (Year: 2018).*
Strop et al., Chemistry and Biology 20: 161-167 (Year: 2013).*
Yu et al., Investigative Ophthalmology & Visual Science 49(2): 522-527 (Year: 2008).*
Kolodych, Sergii et al. "CBTF: New Amine-to-Thiol Coupling Reagent for Preparation of Antibody Conjugates with Increased Plasma Stability", Bioconjugate Chemistry, (2015), vol. 26, No. 2, doi:10.1021/bc500610g, ISSN 1043-1802, pp. 197-200.

(Continued)

*Primary Examiner* — Phuong Huynh
(74) *Attorney, Agent, or Firm* — McDonnell Boehnen Hulbert & Berghoff LLP

(57) ABSTRACT

This invention pertains to protein-drug conjugates that may be used in the treatment of cancers and to pharmaceutical compositions containing the same. The protein-drug conjugate has the following formula (I), wherein: L is a cysteine-containing protein residue linked through one or more of the cysteine groups of the protein, $R_1$ is selected from the group consisting of arylene, arylene-heteroarylene, heteroarylene-arylene and heteroarylene, n is an integer from 0 to 5, p and q are independently 0 or 1, $R_2$, $R_3$ and Z are spacers, u is 0 or 1 and T is a cleavable unit sensitive to hydrolases, k is 1 or 2 and D is a cytotoxic drug residue selected from dolastatin residues, which may be identical to or different from each other when k is 2, m is the mean payload-to-protein ratio (PPR) of the conjugate, which ranges from 0.1 to 16.

$$\left( L - \!\!\left[ S - \overset{\overset{\displaystyle CN}{|}}{C} - R_1 - (R_2)_p - (Z)_n - (R_3)_q - (T)_u - (D)_k \right]\!\! \right)_m \quad (I)$$

17 Claims, 5 Drawing Sheets

(56) References Cited

OTHER PUBLICATIONS

Yao, Houzong et al. "Methods to Design and Synthesize Antibody-Drug Conjugates (ADCs)", International Journal of Molecular Sciences, (2016), vol. 17, No. 2, doi:10.3390/ijms17020194, ISSN 1661-6596, p. 194.
Legigan, Thibaut et al. "Synthesis and Antitumor Efficacy of a . Beta.-Glucuronidase-Responsive Albumin-Binding Prodrug of Doxorubicin", Journal of Medicinal Chemistry, vol. 55, No. 9, doi:10.1021/JM300348R, ISSN 0022-2623, (May 10, 2012), pp. 4516-4520.
Tranoy-Opalinski, Isabelle et al. "[beta]-Glucuronidase-responsive prodrugs for selective cancer chemotherapy: An update", European Journal of Medicinal Chemistry, (2014), vol. 74, doi:10.1016/J.EJMECH.2013.12.045, ISSN 0223-5234, pp. 302-313.
Doronina, Svetlana O. et al. "Development of potent monoclonal antibody auristatin conjugates for cancer therapy", Nature Biotechnology, Gale Group Inc, (2003), vol. 21, No. 7, ISSN 1087-0156, pp. 778-784.
The International Search Report (ISR) with Written Opinion for PCT/EP201062546 dated Oct. 4, 2018, pp. 1-21.

\* cited by examiner

MS spectrum of deglycosylated Compound 25. DAR – Drug-to-Antibody Ratio. Annotation of species: D0 – free antibody; D2 – ADC with DAR 2; D4 – ADC with DAR4; D6 – ADC with DAR6.

HIC chromatogram of Compound 26. Annotation of species: D0 – free antibody; D1 – ADC with DAR 1; D2 – ADC with DAR 2; D3 – ADC with DAR 3; D4 – ADC with DAR 4; D5 – ADC with DAR 5; D6 – ADC with DAR 6; D7 – ADC with DAR 7; D8 – ADC with DAR 8.

MS spectrum of deglycosylated Compound 27. Annotation of species: D0 – free antibody; D2 – ADC with DAR 2; D4 – ADC with DAR4; D6 – ADC with DAR6.

MS spectrum of Compound 32. Annotation of species: D0 – free Albumin; D1 – Albumin conjugate with Drug-to-Protein Ratio = 1.

HIC chromatogram of Compound 33. Annotation of species: D0 – free antibody; D1 – ADC with DAR 1; D2 – ADC with DAR 2; D3 – ADC with DAR 3; D4 – ADC with DAR 4; D5 – ADC with DAR 5; D6 – ADC with DAR 6; D7 – ADC with DAR 7; D8 – ADC with DAR 8.

PROTEIN-DRUG CONJUGATES AND THEIR USE IN THE TREATMENT OF CANCERS

CROSS-REFERENCE TO RELATED APPLICATIONS

This application is a U.S. national phase of International Application No. PCT/EP2018/062546, filed May 15, 2018, which claims priority from European patent application no. 17305563.3, filed May 16, 2017, the disclosures of which are hereby incorporated by reference in their entirety.

FIELD OF THE INVENTION

This invention pertains to protein-drug conjugates that may be used in the treatment of cancers and to pharmaceutical compositions containing the same.

BACKGROUND OF THE INVENTION

Antibody Drug Conjugates (ADCs), also called immunotoxins, are by far the fastest growing class of highly potent active pharmaceutical ingredients. ADC constructs generally involve a recombinant antibody (or antibody-like Fc fusion, monoclonal antibody (MAb) or fragment) covalently attached to one end of a linker group, on the other end of which is a cytotoxin, i.e. a highly potent cell killing toxin (Yao et al. Int. J. Mol. Sci. 2016, 17, 194). The antibody component of the biomolecule provides target specificity. Once the ADC binds to its cell surface antigen/ligand, it enters the cell and the toxin is released, for instance by action of cellular enzymes. The number of adverse effects relative to many other products is thus avoided. For instance, cancer patients treated with tumor-targeted ADCs can generally expect no or less-intense side effects such as hair loss or nausea. Most ADCs are indeed directed to cancer treatment. Besides the marketed trastuzumab emtansine (referred to as T-DM1 or Kadcyla®) and the brentuximab vedotin (Adcetris®), a number of ADCs are currently undergoing clinical trials for a variety of cancer indications.

One of the main prerequisites for the activity of ADCs is the efficient release of the cytotoxic drug upon internalization by cancer cells, while the linker between the antibody and drug should be stable in blood circulation before the ADC reaches its biological target. In this respect, the inventors have already shown that an arylpropiolonitrile linker provided for enhanced plasma stability compared to other linkers (WO 2015/001117; Kolodych et al. *Bioconjugate Chem.* 2015, 26, 197-200). Moreover, a real breakthrough was achieved in the area of specific drug release by the introduction of enzyme-cleavable linkers into the ADC construct, such as a valine-citrulline dipeptide linker (S. O. Doronina et al., *Nat. Biotechnol.*, 2003, 21, 778-84; G. M. Dubrowchik et al., *Bioconjug. Chem.*, 2002, 13, 855-869; US 2009/0324621) and glucuronide linkers (S. C. Jeffrey et al., *Bioconjug. Chem.*, 2006, 17, 831-740; S. C. Jeffrey et al., *ACS Med. Chem. Lett.*, 2010, 1, 277-80; US 2013/0144045; WO 2007/011968). Some of these ADCs have also demonstrated their potential in the treatment of cancer (WO 2015/118497; T. Legigan et al. *J. Med. Chem.* 2012, 55, 4516-4520; I. Tranoy-Opalinski, *Eur. J. Med. Chem.* 2014, 74, 302-313).

However, it would be useful to widen the scope of enzyme-responsive linkers for ADCs and in particular to provide β-galactosidase-sensitive ADCs. Moreover, it would be desirable to provide ADCs with greater plasma stability and/or cellular specificity and/or higher efficacy on tumor volume than known ADCs.

Furthermore, ADCs are characterized by their "drug-to-antibody ratio" (or "DAR"). Their preparation process leads to a mixture of several conjugates differing from each other by their DARs, along with unreacted antibody, such that a mean DAR is usually expressed. Since the DAR determines the amount of payload of drug that can be delivered to a target site, it affects both the safety and efficacy of an ADC. There is thus an increasing regulatory demand for ADCs having more homogeneous DARs. Moreover, it has been known that higher DARs result in aggregates that are detrimental to the ADC efficacy.

It would thus also be desirable to provide ADCs having more specific DARs, i.e. which consist of a mixture of ADCs with a few different DARs only, for instance only even-numbered DARs. Moreover, it is necessary for the process of ADC manufacturing, which includes a chemical reaction between a payload and a recombinant antibody (or antibody-like Fc fusion, mAb or antibody fragment), to be well reproducible and not require laborious optimizations of reaction conditions.

SUMMARY OF THE INVENTION

The present invention is directed to a novel protein-drug conjugate having the following formula (I):

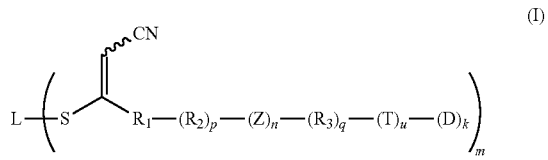

wherein:

L is a cysteine-containing protein residue linked through one or more of the cysteine groups of the protein, $R_1$ is selected from the group consisting of arylene, arylene-heteroarylene, heteroarylene-arylene and heteroarylene, p and q are independently 0 or 1, $R_2$ and $R_3$ are independently selected from the group consisting of —O—, —S—, —C(O)—, —NH—, —C(O)NH—, —NHC(O)—, —C(O)NR$_4$—, —NR$_4$C(O)—, wherein $R_4$ is a solubility unit selected from the group consisting of alkyl, where one or more H is/are substituted by any of the following fragments:

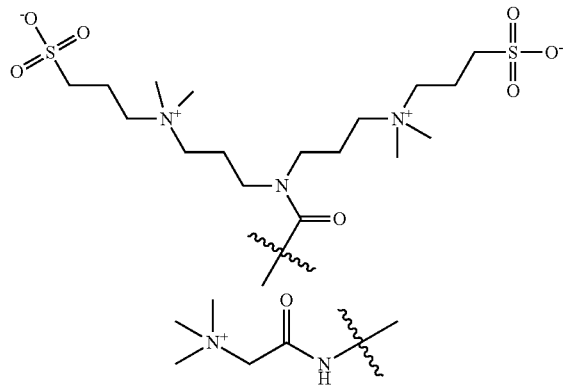

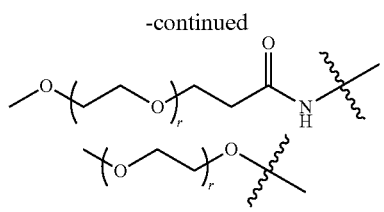

wherein r ranges from 1 to 24,
n is an integer from 0 to 5, preferably from 0 to 2,
Z is a spacer selected from the group consisting of:
a linear or branched, saturated or unsaturated, $C_1$-$C_{22}$ alkylene group optionally interrupted by one or more chemical groups selected from —O—, —S—, —C(O)—, —NH—, —C(O)NH—, —NHC(O)—, —C(O)$NR_4$— or —$NR_4$C(O)— wherein $R_4$ is as defined above,
heteroarylene,
a glycosyl group,
an —O—($CH_2$—$CH_2$—O—)$_t$ or —NH—($CH_2$—$CH_2$—O—)$_t$ group in which t is an integer ranging from 1 to 24,
an amino acid or peptide residue,
wherein the spacers may be identical to or different from each other when n is at least 2,
T is a cleavable unit sensitive to hydrolases,
u is 0 or 1,
k is 1 or 2,
D is a cytotoxic drug residue selected from dolastatin residues, which may be identical to or different from each other when k is 2,
m is the mean payload-to-protein ratio (PPR) of the conjugate, which ranges from 0.1 to 16, preferably 0.1 to 8.

This invention is also directed to these protein-drug conjugates for use as a drug, preferably in the treatment of cancers.

It is further directed to a pharmaceutical composition comprising an effective amount of at least one of these protein drug conjugates and a pharmaceutically acceptable carrier.

This invention still further relates to this pharmaceutical composition for use as a drug, preferably in the treatment of cancer.

BRIEF DESCRIPTION OF THE DRAWINGS

In the attached drawings.

DETAILED DESCRIPTION OF THE INVENTION

Definitions

Figure 1:
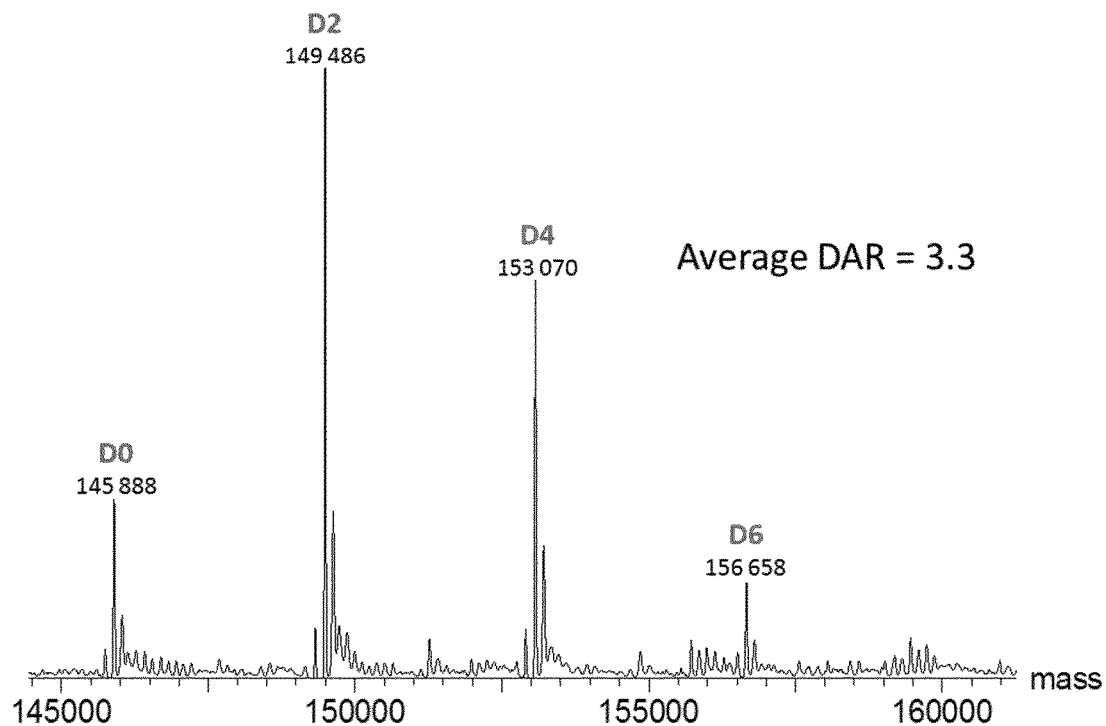
FIG. 1 illustrates the mass spectrum of deglycosylated Compound No. 25 prepared as described in Example 2.

In the present description, the terms used have, unless otherwise indicated, the following meanings:

"alkyl" denotes a linear or branched saturated hydrocarbyl monovalent radical. Among alkyl radicals mention can be made of methyl, ethyl, propyl, isopropyl, butyl, sec-butyl, tert-butyl, pentyl, hexyl, heptyl, octyl, nonyl and decyl radicals;

"alkylene" denotes a linear or branched saturated hydrocarbylene divalent radical. Examples of alkylene groups include methylene, ethylene, propylene, isopropylene, butylene, sec-butylene, tert-butylene, pentylene, hexylene, heptylene, octylene, nonylene and decylene, radicals;

"arylene" denotes a divalent mono- or polycyclic aromatic hydrocarbylene radical, with at least one of the rings having a system of conjugated pi electrons, such as a phenylene or naphtylene group, which may optionally be substituted with up to four groups including, but not limited to: —COOH, —$SO_3H$, —$OCH_3$, —F, —Cl, —Br, —I, —OH, —$NH_2$, —$NO_2$, —CN;

"heteroarylene" refers to a divalent 5 to 14-membered mono- or polycyclic heteroaromatic radical, containing from 1 to 4 heteroatoms, the other atoms being carbon atoms, which may optionally be substituted with up to four groups including, but not limited to: —COOH, —$SO_3H$, —$OCH_3$, —F, —Cl, —Br, —I, —OH, —$NH_2$, —$NO_2$, —CN. The heteroatoms can be oxygen, sulfur or nitrogen atoms. Among heteroarylene radicals, mention can be made of furylene, thienylene, pyridylene, pyrrolylene, pyrimidylene, pyrazinylene, oxazolylene, oxadiazolylene, isoxazolylene, quinolylene, thiazolylene and triazolylene groups, wherein triazolylene groups are preferred;

"arylene-heteroarylene" denotes a divalent radical consisting of an arylene group covalently linked to a heteroarylene group, wherein the arylene group is linked to the —C(S-L)=C—CN group in Formula (I), "heteroarylene-arylene" denotes a divalent radical consisting of an arylene group covalently linked to a heteroarylene group, wherein the heteroarylene group is linked to the —C(S-L)=C—CN group in Formula (I), "glycosyl" denotes any glycosyl group which may in particular be selected from D-glucuronyl, L-iduronyl, D-glucopyranosyl, D-galactopyranosyl, N-acetyl-D-glucosaminyl, N-acetyl D-galactosaminyl, D-mannopyranosyl or L-fucopyranosyl.

"cytotoxic drug residue" denotes a moiety consisting of a cytotoxic drug deprived of one or more atoms of one of its functional groups which has reacted with the remaining of the protein-drug conjugate.

The protein-drug conjugates of this invention have the following formula (I):

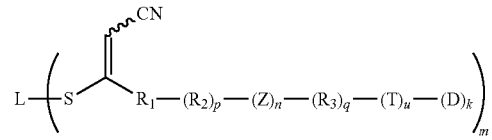

in which a cysteine-containing protein residue L is connected via one of its cysteine groups to one or more drugs D via a specific linker chain comprising a (hetero)arylpropiolonitrile (APN) moiety. In the context of this description, the moiety formed by the linker and the drug(s) attached thereto is designated as "the payload".

In the above formula, m is the mean Payload-to-Protein Ratio of the conjugate, i.e. the mean number of payloads attached per protein. In individual PPR species, this ratio ranges from 0 to 16, preferably from 0 to 8, as measured according to Mass Spectroscopy (MS) spectra and hydrophobic Interaction Chromatography (HIC). The protocol used for measuring the PPR of the ADCs according to this invention is described in the Examples of this application.

Linker Chain

In this linker chain, $R_1$ is selected from the group consisting of arylene, arylene-heteroarylene, heteroarylene-arylene and heteroarylene, preferably arylene or arylene-heteroarylene.

Moreover, $R_2$ and $R_3$ may or not be present (p and q may be independently 0 or 1). If present, $R_2$ and $R_3$ are independently selected from the group consisting of —O—, —S—, —C(O)—, —NH—, —C(O)NH—, —NHC(O)—, —C(O)NR_4—, —NR_4C(O)—, wherein $R_4$ is a solubility unit selected from the group consisting of alkyl, where one or more H is/are substituted by any of the following fragments:

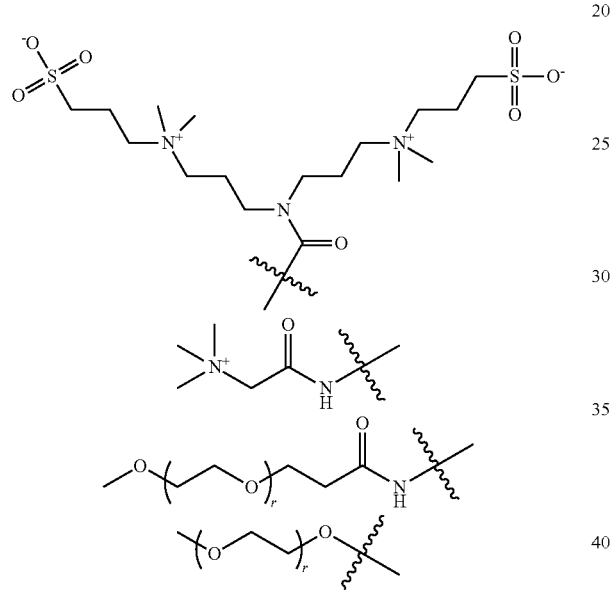

wherein r ranges from 1 to 24,

Moreover, in Formula (I), Z is a spacer selected from the group consisting of:
- a linear or branched, saturated or unsaturated, $C_1$-$C_{22}$ alkylene group optionally interrupted by one or more chemical groups selected from —O—, —S—, —C(O)—, —NH—, —C(O)NH—, —NHC(O)—, —C(O)NR_4— or —NR_4C(O)— wherein $R_4$ is as defined above,
- heteroarylene,
- a glycosyl group,
- an —O—(CH_2—CH_2—O—)_t or —NH—(CH_2—CH_2—O—)_t group in which t is an integer ranging from 1 to 24,
- an amino acid or peptide residue.

No spacer is present in case n is 0. Furthermore, the spacers may be identical to or different from each other when n is in the range from 2 to 5.

Preferred spacers Z for use in this invention are selected from the group consisting of:
- a linear or branched, saturated $C_1$-$C_{22}$ alkylene group optionally interrupted by one or more chemical groups selected from —O— and —C(O)NH—, and
- a heteroarylene group.

In Formula (I), T identifies a cleavable unit sensitive to hydrolases. The hydrolases are preferably intracellular hydrolases and are selected from proteases such as Cathepsin B; peptidases; esterases; and glycosidases such as glucuronidases and galactosidases.

T may for instance be selected from the following groups:

a group which is sensitive to glucuronidases, having the following formula:

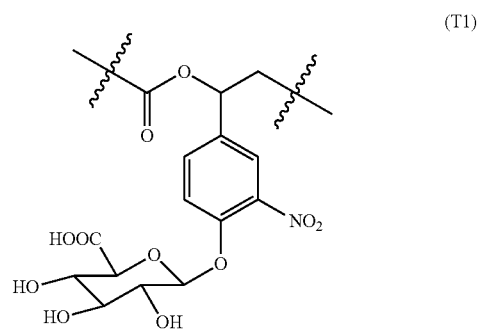 [SMILES: *CC(OC(*)=O)c1ccc(OC2OC(C(=O)O)C(O)C(O)C2O)c([N+](=O)[O-])c1]

(T1)

a group which is sensitive to galactosidases, having the following formula:

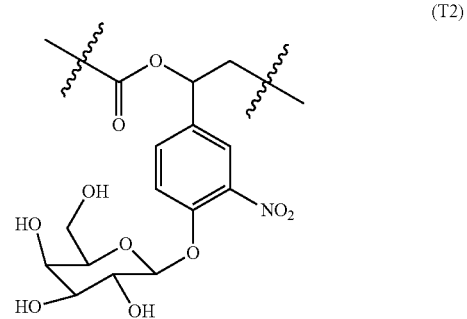 [SMILES: *CC(OC(*)=O)c1ccc(OC2OC(CO)C(O)C(O)C2O)c([N+](=O)[O-])c1]

(T2)

a group which is sensitive to cathepsin B, having the following formula: A-W where A is a di-, tri-, tetra- or pentapeptide residue and W is:

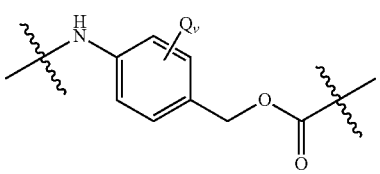

where v is an integer from 0 to 4 and Q is selected from the group consisting of: $C_1$-$C_8$ alkyl, O—($C_1$-$C_8$ alkyl), halogen, nitro and cyano, for instance T is the following group:

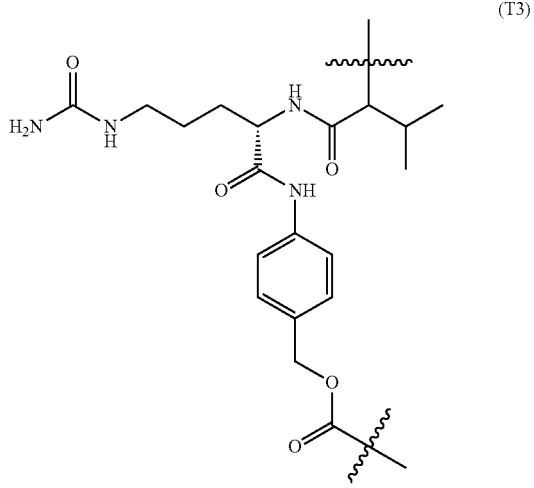 [SMILES: *C(=O)OCc1ccc(NC(=O)[C@H](CCCNC(N)=O)NC(=O)C(*)C(C)C)cc1] (T3)

In any case, the drug is linked to T through the carbonyloxy function of T.

In a preferred embodiment, u is 1. In a more preferred embodiment, u is 1 and T is T3.

According to one embodiment of this invention, the protein-drug conjugate is such that:
$R_1$ is arylene, preferably phenylene,
p is 0 or 1 and $R_2$ is —C(O)NH—,
n is an integer from 0 to 2,
q is 0 or 1 and $R_3$ is selected from the group consisting of —C(O)— and —CONH—,
u is 1.

According to another embodiment of this invention, the protein-drug conjugate is such that:
$R_1$ is arylene-heteroarylene,
p is 0,
n is 1,
q is 1 and $R_3$ is —C(O)NH—,
u is 1 and (T) is preferably (T3).

Protein

In Formula (I) above, L is a cysteine-containing protein residue linked through one or more of its cysteine groups. As used herein, the term "cysteine-containing protein residue" refers to a moiety consisting of a cysteine-containing protein deprived of one or more of its —SH groups and which is linked to the remaining of the ADC by the sulfur atom of these —SH groups.

Preferably, L is a cysteine-containing protein capable to bind to the membrane of a cell, preferably a cancer cell. In particular, L is a protein that binds specifically a molecule present at the membrane of a cancer cell, preferably a molecule selected from the group consisting of proteins, glycoproteins, glycolipids, carbohydrates, or a combination thereof, even more preferably L is a protein that binds specifically a protein present at the membrane of a cancer cell.

The membrane molecule to which the L protein is capable to bind to is a molecule mainly or exclusively present at the membrane of a cancer cell. In a particular embodiment, the membrane molecule recognized by the L protein is a protein overexpressed at the membrane of a cancer cell.

In a preferred embodiment, the L protein is selected from the group consisting of antibodies, ligands, in particular receptor ligands.

In a preferred embodiment, L is an antibody.

In another embodiment, L is albumin, preferably human serum albumin (HSA).

As used herein, the terms "antibody" refers to immunoglobulin molecules and immunologically active portions of immunoglobulin molecules, i.e., molecules that contain an antigen-binding site that immunospecifically binds an antigen. As such, the term antibody encompasses not only whole antibody molecules, but also antigen-binding antibody fragments as well as variants (including derivatives) of antibodies and antibody fragments. In particular, the antibody according to the invention may correspond to a monoclonal antibody (e.g. a chimeric, humanized or human antibody), or a fragment of monoclonal antibody. The term antibody refers to classical antibodies as well as to Heavy-chain antibodies and fragments and derivatives thereof such as (VHH)2 fragments and single domain antibodies.

As used herein, the term "classical antibody" refers to a large Y-shaped glycoprotein that is typically made of two large heavy-chains linked to each other by disulfide bonds, each heavy chain being linked to a smaller light-chain by a disulfide bond. Each chain is composed of structural domains, i.e. immunoglobulin domains. These domains contain about 70-110 amino acids and are classified into variable (IgV), and constant (IgC) domains. Antibodies are capable to recognize a unique molecule, i.e. an antigen, an epitope or a ligand, via its variable regions located at the tip of the "Y" of a classical antibody. In placental mammals there are five classical antibody isotypes known as IgA, IgD, IgE, IgG, and IgM that are classified according to the type of their heavy chains denoted by the Greek letters: α, δ, ε, γ, and μ respectively. Classical antibodies can polymerized, in particular to form dimers or pentamers.

As used herein, the term "heavy chain" refers to a polypeptide constituted of two regions, the constant region formed of three or four immunoglobulin constant domains depending on the type of heavy chain and the variable region formed of a single immunoglobulin variable domain.

As used herein, the term "light chain" refers to a polypeptide constituted of two regions, the constant region formed of a single immunoglobulin constant domains and the variable region formed of a single immunoglobulin variable domain. In mammals there are two types of immunoglobulin light chain, which are called lambda (λ) and kappa (κ).

As used herein the term "variable domain" refers to the immunoglobulin domain of a heavy or of a light chain that is responsible for binding to an antigen. A variable domain comprises several loops referred to as hypervariables or complementarity determining regions (CDRs) which are responsible for binding to the antigen.

As used herein "VH" refers to the variable domain of a heavy chain.

As used herein, the term "Fc (Fragment crystallizable) region" refers to the part of the heavy chain corresponding to the first two or three immunoglobulin constant domain (depending on the type of heavy chain) present at the base of the "Y" in a classical antibody. The Fc region contains a conserved glycosylation site involved in different interactions.

An "antibody fragment" of classical antibodies comprises a portion of an intact antibody, preferably the antigen binding or variable region of the intact antibody. Examples of antibody fragments include Fv, Fab, Fab', F(ab)2, F(ab')2, F(ab)3, Fv (typically the VL and VH domains of a single arm of an antibody), single-chain Fv (scFv), di-scFvs or sc(Fv)2, dsFv, Fd (typically the VH and CH1 domain), dAb (typically a VH domain), CDRs, VH, VL, minibodies, diabodies and multi-specific antibodies formed from antibodies fragments.

The term "Fab" denotes an antibody monovalent fragment having a molecular weight of about 50,000 and antigen binding activity, and consisting of the light and heavy chains variable domains (VL and VH), the light chain constant domain (CL) and the first heavy chain constant domain (CH1) domains which can be obtained by cutting a disulfide bond of the hinge region of the F(ab')2 fragment.

The term "Fv" refers to the N-terminal part of the Fab fragment and consists of the variable portions of a light chain and a heavy chain.

The term "F(ab')2" refers to an antibody bivalent fragment having a molecular weight of about 100,000 and antigen binding activity, which comprises two Fab fragments linked by a disulfide bridge at the hinge region.

The term "Fd" refers to an antibody fragment consisting of the VH and CH1 domains.

The term "dAb" (Ward et al., 1989 Nature 341:544-546) refers to a single variable domain antibody, i.e. an antibody fragment which consists of a VH or VL domain. A single chain Fv ("scFv") polypeptide is a covalently linked VH::VL heterodimer which is usually expressed from a gene fusion including VH and VL encoding genes linked by a peptide-encoding linker. "dsFv" is a VH::VL heterodimer stabilised by a disulfide bond. Divalent and multivalent antibody fragments can form either spontaneously by association of monovalent scFvs such as di-scFvs, or can be generated by coupling monovalent scFvs by a peptide linker, such as divalent sc(Fv)2.

The term "diabodies" refers to small antibody fragments with two antigen-binding sites, which fragments comprise a VH domain connected to a VL domain in the same polypeptide chain (VH-VL). By using a linker that is too short to allow pairing between the two domains on the same chain, the domains are forced to pair with the complementarity domains of another chain and create two antigen-binding sites. The diabody may be mono- or bi-specific.

Antibody fragments which recognize specific epitopes can be generated by known techniques. The antibody fragments are antigen binding portions of an antibody, such as F(ab')2, Fab, Fv, scFv and the like. Other antibody fragments include, but are not limited to: the F(ab')2 fragments which can be produced by pepsin digestion of the antibody molecule and the Fab' fragments, which can be generated by reducing disulfide bridges of the F(ab')2 fragments. Alternatively, Fab' expression libraries can be constructed (Huse et al., 1989, Science, 246:1274-1281) to allow rapid and easy identification of monoclonal Fab' fragments with the desired specificity.

As used herein, the terms "Heavy-chain antibody" or "HCAbs" refer to immunoglobulins that are devoid of light chains and consist in two heavy chains. These antibodies do not rely upon the association of heavy and light chain variable domains for the formation of the antigen-binding site but instead the variable domain of the heavy polypeptide chains alone naturally forms the complete antigen binding site. Each heavy chain comprises a constant region and a variable domain which enables the binding to a specific antigen, epitope or ligand. As used herein, HCAbs encompass heavy chain antibodies of the camelid-type in which each heavy chain comprises a variable domain called VHH and two constant domains. Such heavy-chain antibodies directed against a specific antigen can be obtained from immunized camelids. Camelids encompass dromedary, camel, lama and alpaca. Camelid HCAbs have been described by Hamers-Casterman et al., Nature, 1993, 363: 446. Other examples of HCAb are immunoglobulin-like structures (Ig-NAR) from cartilaginous fishes. Heavy-chain antibodies can be humanized using well-known methods.

The terms "single domain antibody", "sdAb" and "nanobody" are used interchangeably and have the same meaning. As used herein, the term single domain antibody refers to a single variable domain derived from a heavy chain antibody, which is able to bind an antigen, an epitope or a ligand alone, that is to say, without the requirement of another binding domain. A single domain antibody may be or may derive from VHH and V-NAR. V-NAR refers to the variable domain found in immunoglobulin-like structures (Ig-NAR) discovered in cartilaginous fishes such as sharks. As an alternative, single domain antibody may be obtained from human VH by camelization, in particular with F37, E44, R45 and F47 mutations. For review about single domain antibodies, one may refer to Saerens et al., *Current Opinion in Pharmacology*, 2008, 8:600-608. In a preferred embodiment, the single domain antibody according to the invention is a synthetic single domain antibody.

As used herein, the term "synthetic" means that such antibody has not been obtained from fragments of naturally occurring antibodies but produced from recombinant nucleic acids comprising artificial coding sequences (cf. WO 2015/063331).

The term "VHH", as used herein, refers to an antibody fragment consisting of the VH domain of camelid heavy-chain antibody. VHH fragments can be produced through recombinant DNA technology in a number of microbial hosts (bacterial, yeast, mould), as described in WO 94/29457. Alternatively, binding domains can be obtained by modification of the VH fragments of classical antibodies by a procedure termed "camelization", described by Davies et al, 1995. Dimers of VHH fragments, i.e. (VHH)2, can be generated by fusing two sequences encoding VHH fragments, end to end, e.g. by PCR. Preferably, the (VHH)2 fragment is monospecific. The two VHH of a (VHH)2 may also recognize two different antigen, i.e. the (VHH)2 may be bispecific.

The variable domain of an antibody of the invention comprises at least three complementarity determining region (CDR) which determines its binding specificity. Preferably, in a variable domain, the CDRs are distributed between framework regions (FRs). The variable domain thus contains at least 4 framework regions interspaced by 3 CDR regions, resulting in the following typical antibody variable domain structure: FR1-CDR1-FR2-CDR2-FR3-CDR3-FR4. CDRs and/or FRs of the single domain antibody of the invention may be fragments or derivatives from a naturally-occurring antibody variable domain or may be synthetic.

A "humanized antibody" is a chimeric, genetically engineered, antibody in which the CDRs from an antibody, e.g. a mouse antibody (donor antibody), are grafted onto a human antibody (acceptor antibody). Thus, a humanized antibody is an antibody having CDRs from a donor antibody and variable region framework and constant regions, when present, from a human antibody.

Likewise, a "camelized antibody" is an antibody having CDRs from a donor antibody, preferably a human donor, and variable region framework and constant regions, when present, from a Camelid antibody.

The term "monoclonal antibody" or "mAb" as used herein refers to an antibody molecule of a single amino acid composition, that is directed against a specific antigen and which may be produced by a single clone of B cells or hybridoma, or by recombinant methods. The use of antibody components derived from humanized monoclonal antibodies obviates potential problems associated with the immunogenicity of murine constant regions. Rodent monoclonal antibodies to specific antigens may be obtained by methods known to those skilled in the art. (See, e.g., Kohler and Milstein, *Nature* 256: 495 (1975), and Coligan et al. (eds.), *Current Protocols In Immunology*, VOL. 1, pages 2.5.1-2.6.7 (John Wiley & Sons 1991)).

Antibodies according to the invention may be produced by any technique known in the art, such as, without limitation, any chemical, biological, genetic or enzymatic technique, either alone or in combination. The antibodies of the invention can be obtained by producing and culturing hybridomas. See also WO 2015/063331 for the production of synthetic single domain antibodies.

The antibody according to the invention can be any kind of antibody. In particular, the antibody can comprise, consist or consist essentially in a classical Y-shaped antibody with two heavy chains and light chains or a fragment thereof. Preferably said fragment comprises the antigen binding or variable region of the antibody. Said fragment may be selected, without limitation, from the group consisting in Fv, Fab, Fab', F(ab)2, F(ab')2, F(ab)3, Fv, single-chain Fv (scFv), di-scFvs or sc(Fv)2, dsFv, Fd, dAb, CDRs, VH, VL, minibodies, diabodies, and multi-specific antibodies formed from antibodies fragments.

The antibody according to the invention can also comprise, consist or consist essentially in a heavy-chain antibody. Preferably a heavy-chain antibody is selected from the heavy-chain antibodies from camelids or from cartilaginous fishes. More preferably, the antibody is a heavy-chain antibody derived from camelids. Camelids antibody encompasses in particular dromedary, camel, lama and alpaca. Preferably, the antibody is a heavy-chain antibody derived from lama.

In a preferred embodiment, the antibody comprises, consists, or consists essentially in a single domain antibody or a fragment thereof. The single domain antibody can derive from a VHH or a V-NAR, preferably from a VHH. In particular, the antibody according to the invention can be a humanized single domain antibody, in particular a humanized VHH, or a fragment thereof.

Preferably, said fragment of the single domain antibody comprises the three CDRs.

Optionally, the antibody according to the invention is a single domain antibody fused to an Fc region, preferably an Fc region selected from the group consisting in IgA, IgD, IgE, IgG, and IgM Fc regions, more preferably an IgG Fc region.

Preferably, the Fc region is selected from human, mouse and rabbit Fc regions. Even more preferably, the antibody according to the invention is a single domain antibody fused to a human Fc region, even more preferably a single domain antibody fused to a human IgG Fc region.

The antibody according to the invention may be a monomeric antibody or a multimeric antibody. In particular, the antibody according to the invention may be a monomeric antibody.

The antibody according to the invention may also be a multimeric antibody. When the antibody is a multimeric classical Y-shape antibody, it is preferably a dimer or a pentamer. Alternatively, the antibody is a multimeric single domain antibody, preferably a dimerized single domain antibody.

In a multimeric antibody, the variable domains of the different monomers can be identical (i.e. homomeric) or different (i.e heteromeric). Preferably, the multimeric antibody according to the invention is homomeric. When the multimeric antibody according to the invention is heteromeric, the variable domains of the different monomers can all bind the same protein. Alternatively, they can bind different proteins.

The antibody according to the invention can be monoclonal or polyclonal. Preferably, the antibody according to the invention is monoclonal.

The antibody according to the invention comprises at least a variable domain. It may comprise several variable domains, in particular when the antibody is multimeric.

In a preferred embodiment the antibody according to the invention is selected from the group consisting of trastuzumab, bevacizumab, cetuximab, panitumumab, ipilimumab, rituximab, alemtuzumab, ofatumumab, gemtuzumab, brentuximab, ibritumomab, tositumomab, pertuzumab, adecatumumab, IGN101, labetuzumab, hua33, pemtumomab, oregovomab, minretumomab (CC49), cG250, J591, MOv-18, farletuzumab (MORAb-003), 3F8, ch14,18, KW-2871, hu3S193, IgN311, IM-2C6, CDP-791, etaracizumab, volociximab, nimotuzumab, MM-121, AMG 102, METMAB, SCH 900105, AVE1642, IMC-A12, MK-0646, R1507, CP 751871, KB004, III A4, map atumumab , HGS-ETR2, CS-1008, denosumab, sibrotuzumab, F19, 81C6, pinatuzumab, lifastuzumab, glembatumumab, coltuximab, lorvotuzumab, indatuximab, anti-PSMA, MLN-0264, ABT-414, milatuzumab, ramucirumab, abagovomab, abituzumab, adecatumumab, afutuzumab, altumomab pentetate, amatuximab, anatumomab, anetumab, apolizumab, arcitumomab, ascrinvacumab, atezolizumab, bavituximab, bectumomab, belimumab, bivatuzumab, brontictuzumab, cantuzumab, capromab, catumaxomab, citatuzumab, cixutumumab, clivatuzumab, codrituzumab, conatumumab, dacetuzumab, dallotuzumab, daratumumab, demcizumab, denintuzumab, depatuxizumab, derlotuximab, detumomab, dinutuximab, drozitumab, duligotumab, durvalumab, dusigitumab, ecromeximab, edrecolomab, elgemtumab, emactuzumab, enavatuzumab emibetuzumab, enfortumab, enoblituzumab, ensituximab, epratuzumab, ertumaxomab, etaracizumab, farletuzumab, ficlatuzumab, figitumumab, flanvotumab, futuximab, galiximab, ganitumab, icrucumab, igovomab, imalumab, imgatuzumab, indusatumab, inebilizumab, intetumumab, iratumumab, isatuximab, lexatuzumab, lilotomab, lintuzumab, lirilumab, lucatumumab, lumretuzumab, margetuximab, matuzumab, mirvetuximab, mitumomab, mogamulizumab, moxetumomab, nacolomab, naptumomab, narnatumab, necitumumab, nesvacumab, nimotuzumab, nivolumab, nofetumomab, obinutuzumab, ocaratuzumab, ofatumumab, olaratumab, onartuzumab, ontuxizumab, oportuzumab, oregovomab, otlertuzumab, pankomab, parsatuzumab, pasotuxizumab, patritumab, pembrolizumab, pemtumomab, pidilizumab, pintumomab, polatuzumab, pritumumab, quilizumab, racotumomab, ramucirumab, rilotumumab, robatumumab, sacituzumab, samalizumab, satumomab, seribantumab, siltuximab, sofituzumab, tacatuzumab, taplitumomab, tarextumab, tenatumomab, teprotumumab, tetulomab, ticilimumab, tigatuzumab, tositumomab, tovetumab, tremelimumab, tucotuzumab, ublituximab, ulocuplumab, urelumab, utomilumab, vandortuzumab, vantictumab, vanucizumab, varlilumab, veltuzumab, vesencumab, volociximab, vorsetuzumab votumumab, zalutumumab, zatuxima, combination and derivatives thereof.

Preferably, the antibody according to the invention is IgG, preferably subtypes IgG1 or IgG4, for example trastuzumab or rituximab.

Drug

The drug according to the invention is a cytotoxic drug. As used herein, the term "cytotoxic drug" refers to a molecule that when entering in contact with a cell, optionally upon internalization into the cell, alters a cell function (e.g. cell growth and/or proliferation and/or differentiation and/or metabolism such as protein and/or DNA synthesis) in a detrimental way or leads to cell death. As used herein, the term "cytotoxic drug" encompasses toxins, in particular cytotoxins. In principle, a cytotoxic drug is defined as a LO1 ATC molecule ("Anatomical Therapeutic Chemical Classification System" where LO1 is a subgroup defining antineoplastic and immunomodulating agents defined by WHO Collaborating Centre for Drug Statistics Methodology).

The cytotoxic drug according to the invention is selected from dolastatins such as dolastin 10, dolastin 15, auristatin E, auristatin EB (AEB), auristatin EFP (AEFP), monomethyl auristatin F (MMAF), monomethylauristatin-D (MMAD), monomethyl auristatin E (MMAE), and 5-benzoylvaleric acid-AE ester (AEVB).

Preferably, the cytotoxic drug according to the invention is selected from the group consisting of MMAF, MMAD and MMAE.

More preferably, the cytotoxic drug according to the invention is MMAE.

Preparation Process

The compounds of this invention may be synthetized by reacting a payload comprising the linker and drug with a cysteine residue of a protein, for instance with a partially reduced monoclonal antibody, as described in the following Examples.

The synthesis of a number of payloads is also described in the following Examples and may be easily adapted by the skilled person to the preparation of further ADCs according to this invention.

Uses

The compounds of formula (I) may be used as drugs, preferably in the treatment of cancers.

The term "cancer" or "tumor", as used herein, refers to the presence of cells possessing characteristics typical of cancer-causing cells, such as uncontrolled proliferation, and/or immortality, and/or metastatic potential, and/or rapid growth and/or proliferation rate, and/or certain characteristic morphological features. This term refers to any type of malignancy (primary or metastases) in any type of subject. It may refer to solid tumor as well as hematopoietic tumor.

Preferably, the cancer according to the invention is selected from the group consisting of the prostate cancer, the lung cancer, the breast cancer, the gastric cancer, the kidney cancer, the ovarian cancer, the hepatocellular cancer, the osteosarcoma, the melanoma, the hypopharynx cancer, the esophageal cancer, the endometrial cancer, the cervical cancer, the pancreatic cancer, the liver cancer, the colon or colorectal cancer, the neuroendocrine tumors, the malignant tumor of the muscle, the adrenal cancer, the thyroid cancer, the uterine cancer, the skin cancer, the bladder cancer, the head and neck cancer, the lymphoma, and the leukemia.

Examples of cancers that may be treated with antibody-drug conjugates of this invention are listed in the table below.

| Antibody | Cancer type |
| --- | --- |
| Rituximab | Non-Hodgkin's lymphome |
| Tositumomab | Lymphome |
| Brentuximab | Hodgkin's lymphome |

-continued

| Antibody | Cancer type |
| --- | --- |
| Gemtuzumab | Acute myelogenous leukemia |
| Alemtuzumab | Chronic lymphocytic leukemia |
| Adecatumumab | Breast, colon and lung cancers |
| Labetuzumab | Breast, colon and lung cancers |
| hua33 | Colorectal carcinoma |
| Pemtumomab | Breast, colon, ovarian and lung cancers |
| Minretumomab | Breast, colon and lung cancers |
| cG250 | Renal cell carcinoma |
| J591 | Prostate carcinoma |
| Farletuzumab | Ovarian tumours |
| 3F8, ch14 and KW-2871 | Neuroectodermal tumours |
| hu3 S193 and IgN311 | Breast, colon, prostate and lung cancers |
| Cetuximab and nimotuzumab | Glioma, colon, lung, breast, head and neck tumours |
| Trastuzumab and pertuzumab | Breast, colon, ovarian, prostate and lung cancers |
| MM-121 | Breast, colon, ovarian, prostate and lung cancers |
| AMG102 | Breast, ovarian and lung cancers |
| AVE1642 | Glioma, lung, breast, head and neck, prostate and thyroidis cancers |
| KB004 | Lung, kidney and colon tumours, melanoma, glioma and haematological maligancies |
| Denosumab | Prostate cancer and bone metastases |
| Sibrotuzumab | Colon, breast, lung, pancreas and head and neck tumours |
| B1C6 | Glioma, breast and prostate tumours |

The compounds of this invention particularly aim at treating breast, colon, ovarian, prostate and lung cancers.

As used herein, the term "treatment", "treat" or "treating" refers to any act intended to ameliorate the health status of patients such as therapy, prevention, prophylaxis and retardation of the disease. In certain embodiments, such term refers to the amelioration or eradication of a disease or symptoms associated with a disease. In other embodiments, this term refers to minimizing the spread or worsening of the disease resulting from the administration of one or more therapeutic agents to a subject with such a disease.

As used herein, the terms "subject", "individual" or "patient" are interchangeable and refer to an animal, preferably to a mammal, even more preferably to a human. However, the term "subject" can also refer to non-human animals, in particular mammals. The subject according to the invention is an animal, preferably a mammal, even more preferably a human. The subject may be a non-human animal, in particular selected from mammals such as dogs, cats, horses, cows, pigs, sheep and non-human primates, among others. Preferably, the subject is human, preferably an adult, more preferably an adult of at least 40 years old, still more preferably an adult of at least 50 years old, even more preferably an adult of at least 60 years old.

For the purpose of treating cancers, the compounds of this invention are usually delivered in a pharmaceutical composition comprising an effective amount of at least one of the claimed compounds and a pharmaceutically acceptable carrier.

As used herein, the term "pharmaceutically acceptable carrier" refers to any ingredient except active ingredients (namely excipients) that is present in a pharmaceutical composition. Its addition may be aimed at conferring a particular consistency or other physical or gustative properties to the final product. An excipient or pharmaceutically acceptable carrier must be devoid of any interaction, in particular chemical, with the actives ingredients. Conventional excipients can be used according to techniques well known by those skilled in the art.

The compound of formula (I) is typically included in an effective amount in a pharmaceutical composition.

As used herein, the term "effective amount" refers to a quantity of an active ingredient, which prevents, removes or reduces the deleterious effects of the disease.

The invention also relates to the use of a protein-drug conjugate according to the invention or a pharmaceutical composition according to the invention, for the preparation of a medicament. Preferably, it relates to a protein-drug conjugate according to the invention or a pharmaceutical composition according to the invention, for the preparation of a medicament for treating cancer in a subject.

It further relates to a method for treating in a subject a cancer, wherein a therapeutically effective amount of a protein-drug conjugate according to the invention or a therapeutically effective amount of a pharmaceutical composition according to the invention, is administered to said subject suffering from a cancer.

The protein-drug conjugate according to the invention or the pharmaceutical composition according to the invention may be administered by any convenient route to a subject in need thereof. For instance, it can be administered by a systemic route, in particular by subcutaneous, intramuscular, intravenous or intradermal, preferably by intravenous, injection.

The protein-drug conjugate according to the invention or the pharmaceutical composition according to the invention may be administered as a single dose or in multiple doses.

The protein-drug conjugate according to the invention or the pharmaceutical composition according to the invention may be administered between every day and every month, preferably every week or every two weeks, more preferably every week.

The duration of treatment with a protein-drug conjugate according to the invention, or with a pharmaceutical composition according to the invention, is preferably comprised between 1 and 20 weeks, preferably between 1 and 10 weeks. Alternatively, the treatment may last as long as the symptoms of the disease persist.

The amount of protein-drug conjugate according to the invention or of pharmaceutical composition according to the invention to be administered has to be determined by standard procedure well known by those of ordinary skills in the art. Physiological data of the patient (e.g. age, size, and weight) and the routes of administration have to be taken into account to determine the appropriate dosage, so as a therapeutically effective amount will be administered to the patient.

This invention will be better understood in light of the following examples, which are provided for illustrative purposes only.

EXAMPLES

Materials

All reagents were obtained from commercial sources and used without prior purifications. Dry solvents were obtained from Sigma-Aldrich.

Instrumentation $^1$H and $^{13}$C NMR spectra were recorded at 25° C. on Bruker 400 spectrometer. Recorded shifts are reported in parts per million (δ) and calibrated using residual non-deuterated solvent. Data are represented as follow: chemical shift, multiplicity (s=singlet, d=doublet, t=triplet, q=quartet, quint=quintet, m=multiplet, br=broad), coupling constant (J, Hz) and integration.

High resolution mass spectra (HRMS) were obtained using Agilent Q-TOF (time of flight) 6520 coupled to Agilent 1200 HPLC with Diode Array Detector; low resolution mass spectra, using Agilent MSD 1200 SL (ESI/APCI) coupled to Agilent 1200 HPLC with Diode Array Detector.

IR spectra were recorded on a Nicolet 380 FT-IR spectrometer from Thermo Electron Corporation as a DCM solution or solid on a diamond plate.

The semi-preparative HPLC system consisted of two Shimadzu LC-8A pumps, an SPD-10A VP detector (Shimadzu), an SCL-10A VP controller (Shimadzu), an SIL-10A autosampler, a 2 mL sample loop and a SunFire C18 column (150 mm×19 mm i.d., 5 µm, Waters).

Hydrophobic Interaction Chromatography (HIC) was performed using a liquid chromatography system (Alliance HPLC, Waters, Manchester, UK) coupled to a 2487 UV/visible detector (Waters, Manchester, U.K.). Analyses were realized on a TSKButyl-NPR, 3.5×4.6 mm column (Tosoh Bioscience, Tokyo, Japan) set at room temperature. The mobile phase A consisted of 1.5 M ammonium sulfate, 25 mM potassium phosphate pH 7.0, and the mobile phase B consisted of a mixture 25 mM potassium phosphate and 25% isopropanol at pH 7.0. Separation was obtained with a linear gradient of 10-100% B over 12 min at flow rate of 0.8 mL/min. Analysis were obtained by injecting 10 µg of sample diluted at 1 mg/mL with mobile phase A and integrating the UV area at 210 nm for each species.

Example 1

Synthesis of Payloads

General Procedure B (Applicable to the Synthesis of 11, 23)

To the solution of 9 (1.2 eq.) in dry DMF (30 µL per gmol of 9) was added 2-bromo-1-ethyl-pyridinium tetrafluoroborate (1.2 eq.). The resulting mixture was incubated at 21° C. for 5 min and then amine precursor (e.g. compounds 10, 22) and N,N-diisopropylethylamine (5 eq.) were added. The resulting mixture was stirred at 21° C. for 30 min and the crude product was purified by preparative HPLC (Method A1) and lyophilized to yield pure product.

General Procedure C (Applicable to the Synthesis of 15, 18, 21, 34)

To the solution of 1 eq. of the amine precursor (e.g. compounds 14, 17, 20) in dry DMF (30 µL per gmol of substrate) was added 3 (1 eq.) followed by DIEA (5 eq.) and the mixture was incubated at room temperature for 1 hour. The resulting mixture was purified by preparative HPLC (Method A1) and lyophilized to yield pure product.

Method A1: Preparative High-Performance Liquid Chromatography

The purification was performed on the preparative HPLC system, which consisted of two Shimadzu LC-8A pumps, an SPD-10A VP detector (Shimadzu), an SCL-10A VP controller (Shimadzu), an SIL-10A autosampler, a 2 mL sample loop and a SunFire C18 column (150 mm×19 mm i.d., 5 µm, Waters). Injection volume: 0.5 mL. Gradient elution with a mixture of (A) water/0.05% trifluoroacetic acid and (B) acetonitrile (gradient: 5% B:95% A up to 95% B:5% A over 40 min, 95% B:5% A for 5 min) with a 17 ml/min flow rate.

Compound 4

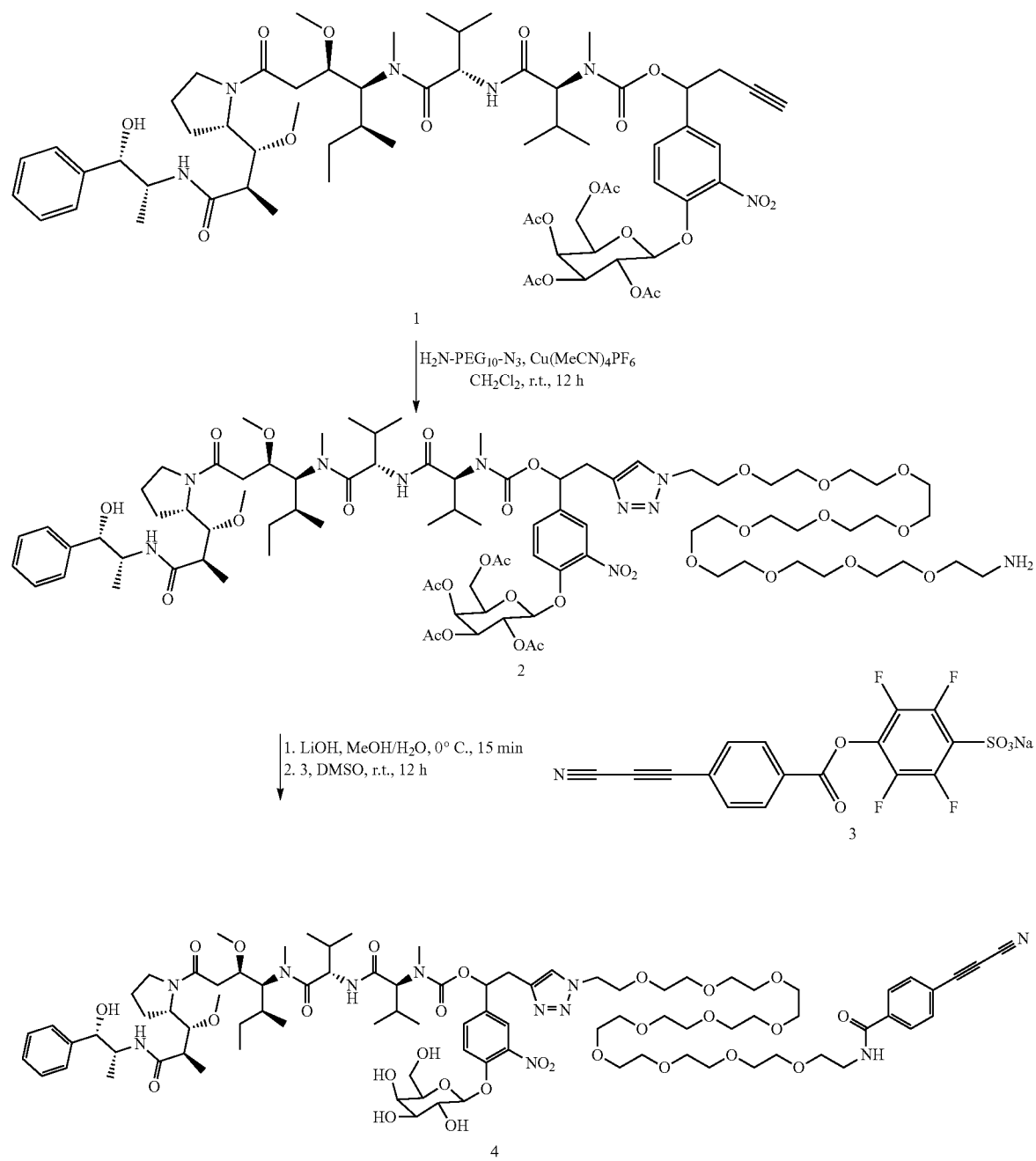

To a solution of 1 (28 mg, 0.0218 mmol) and O-(2-aminoethyl)-O'-(2-azidoethyl)nonaethylene glycol (12.6 mg, 0.024 mmol, 1.1 eq) in $CH_2Cl_2$ (1.8 mL) was added $Cu(MeCN)_4PF_6$ (12.2 mg, 0.0327 mmol). The mixture was stirred at room temperature for 12 h. A solution of disodium EDTA (0.13 g) in $H_2O$ (2.1 mL) was added. The resulting mixture was stirred for 2 h and extracted with $CH_2Cl_2$ (3×50 mL). The combined organic layers were dried over $MgSO_4$ and concentrated in vacuo. The crude product was purified by column chromatography over silica gel (gradient elution 2% to 10% MeOH in $CH_2Cl_2$) to give amine 2 (18.9 mg, 0.0104 mmol, 48%) that was engaged directly in the next step. 2 was dissolved in MeOH (0.8 mL). The mixture was cooled at 0° C. and a solution of lithium hydroxide monohydrate (3.9 mg, 0.0915 mmol) in water (0.8 mL) was added dropwise. The mixture was stirred for 15 min, neutralized with IRC-50 acidic resin, filtrated and concentrated in vacuo. The crude product was then dissolved in DMSO (0.5 mL) and compound 3 (1.2 eq, 3.9 mg) was added. The mixture was stirred at room temperature for 12 h and the solvent was removed under reduced pressure. Finally, the crude product was purified by preparative HPLC (Method A1) to give compound 4 (27.8 mg, 71%).

HRESI-MS: m/z 1814.9204 (calcd. for $C_{88}H_{133}N_{11}O_{28}Na$ 1814.9214 [M+Na]$^+$).

Compound 7

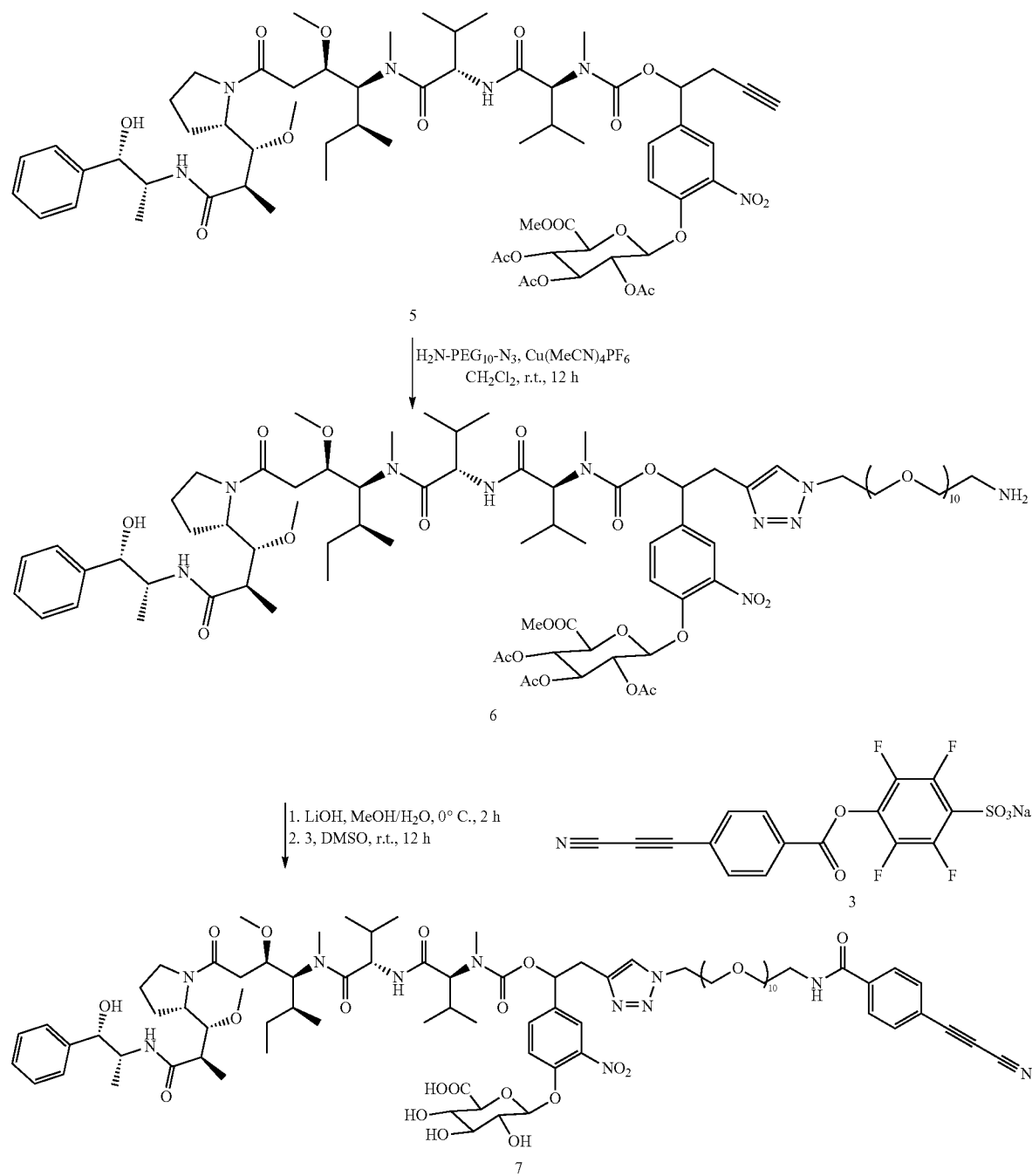

To a solution of 1 (43.6 mg, 0.0348 mmol) and O-(2-aminoethyl)-O'-(2-azidoethyl)nonaethylene glycol (20.2 mg, 0.038 mmol, 1.1 eq) in $CH_2Cl_2$ (2.9 mL) was added $Cu(MeCN)_4PF_6$ (19.5 mg, 0.0523 mmol). The mixture was stirred at room temperature for 12 h. A solution of disodium EDTA (0.21 g) in $H_2O$ (3.4 mL) was added. The resulting mixture was stirred for 2 h and extracted with $CH_2Cl_2$ (3×50 mL). The combined organic layers were dried over $MgSO_4$ and concentrated in vacuo. The crude product was purified by column chromatography over silica gel (gradient elution 2% to 10% MeOH in $CH_2Cl_2$) to give amine 6 (18.7 mg, 0.0149 mmol, 43%) that was engaged directly in the next step. 6 was dissolved in MeOH (0.8 mL). The mixture was cooled at 0° C. and a solution of lithium hydroxide monohydrate (6.3 mg, 0.149 mmol) in water (1.2 mL) was added dropwise. The mixture was stirred for 15 min, neutralized with IRC-50 acidic resin, filtrated and concentrated in vacuo. The crude product was then dissolved in DMSO (0.7 mL) and compound 3 (1.2 eq, 7.5 mg) was added. The mixture was stirred at room temperature for 2 h and the solvent was removed under reduced pressure. Finally, the crude product was purified by preparative HPLC (Method A1) to give compound 7 (20.2 mg, 32%).

HRESI-MS: m/z 1806.9179 (calcd. for $C_{88}H_{132}N_{11}O_{29}$ 1806.9187 $[M+H]^-$).

Compound 8

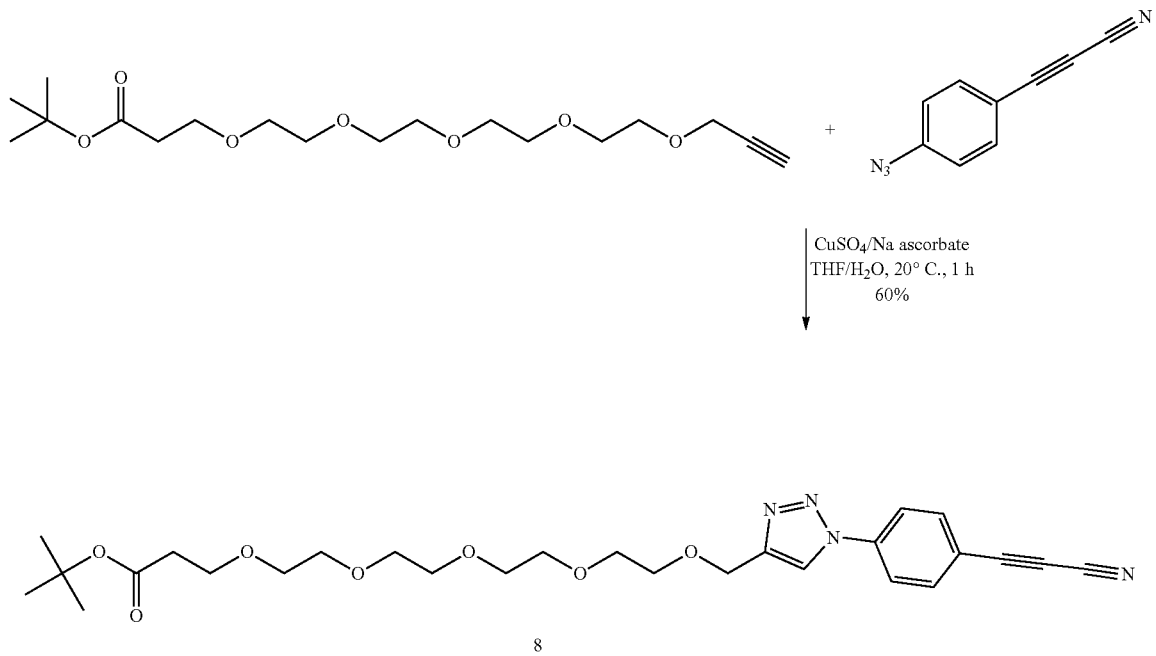

3-(4-azidophenyl)prop-2-ynenitrile (1 eq., 1120 mg, 6.66 mmol) and tert-butyl 4,7,10,13,16-pentaoxanonadec-18-ynoate (1 eq., 2400 mg, 1 mL, 6.66 mmol) were dissolved in THF (25 mL) and water (5 mL) was added to the mixture. To the obtained solution were added CuSO$_4$ (100 mg, 0.627 mmol) in water (0.5 mL) and sodium ascorbate (400 mg, 2.02 mmol) in water (1 mL). The reaction mixture stirred for 5 minutes and another portion of CuSO$_4$ (100 mg, 0.627 mmol) and sodium ascorbate (400 mg, 2.02 mmol) were added to the reaction mixture. To the resulting solution was added the same volume of saturated solution of NH$_4$Cl, the organic fraction was separated, and water phase was extracted three times with ethyl acetate. Combined organic layers were dried over MgSO$_4$, evaporated, and the crude product was purified by flash chromatography (Cyclohexane/EtOAc:100/0 to 0/100 gradient) to give compound 8 (2.11 g, 4 mmol, 60%) as a yellowish oil.

$^1$H NMR (400 MHz, CDCl$_3$) δ=8.14 (s, 1H), 7.88 (d, J=8.3 Hz, 2H), 7.79 (d, J=8.3 Hz, 2H), 4.79 (s, 2H), 3.81-3.55 (m, 18H), 2.49 (t, J=6.5 Hz, 2H), 1.44 (s, 9H). MS (ESI) m/z: 529.1 [M+H]$^+$.

Compound 9

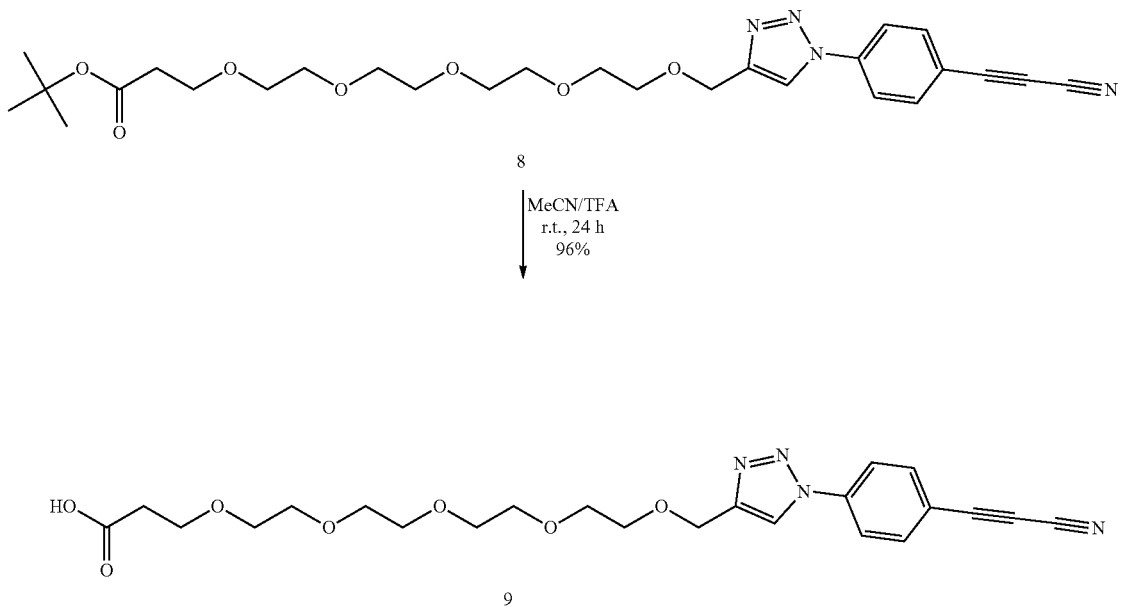

To a solution of 8 (1 eq., 1.77 g, 3.35 mmol) in acetonitrile (50 mL) was added trifluoroacetic acid (20 eq., 7.64 g, 4.97 mL, 67 mmol). The resulting reaction mixture was incubated for 5 days at room temperature. Solvents were evaporated and 100 mL of EtOAc were added. The organic layer was washed with water (3×50 mL), brine (1×50 mL), dried over MgSO$_4$ and evaporated to yield the compound 9 (1250 mg, 2.65 mmol, 79%) as a yellowish oil.

$^1$H NMR (400 MHz, CDCl$_3$) δ=8.29 (s, 1 H), 7.91 (d, J=8.0 Hz, 2H), 7.79 (d, J=8.0 Hz, 2H), 4.81 (s, 2H), 3.83-3.53 (m, 18H), 2.58 (t, J=5.6 Hz, 2H). MS (ESI) m/z: 473.0 [M+H]$^+$.

Compound 11

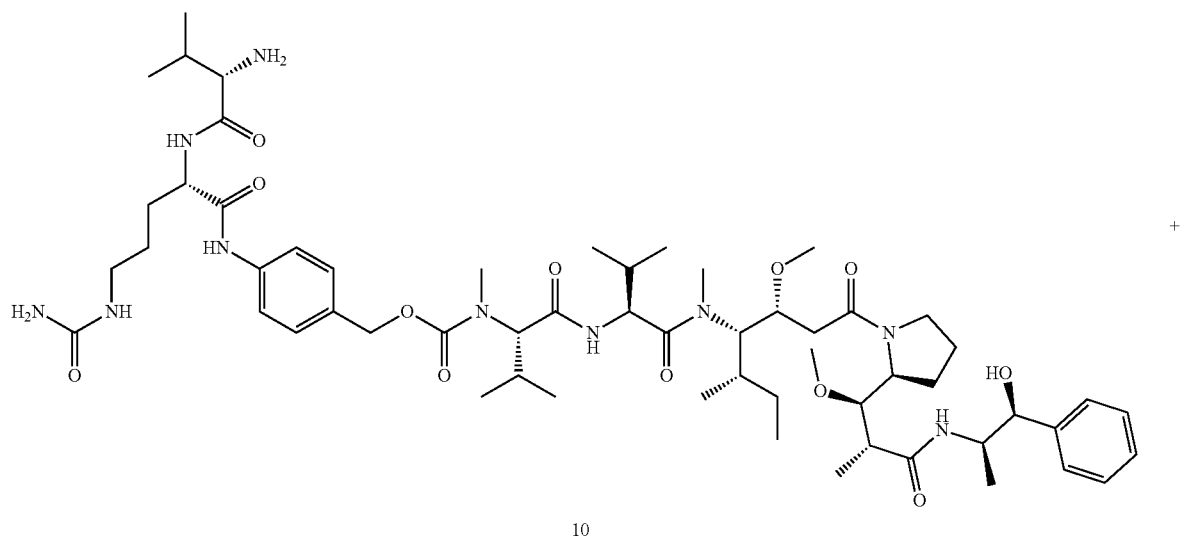

10

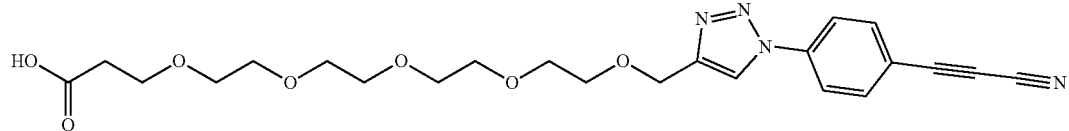

9

| BEP/DIEA
DMF, 1 h, 20° C
49%

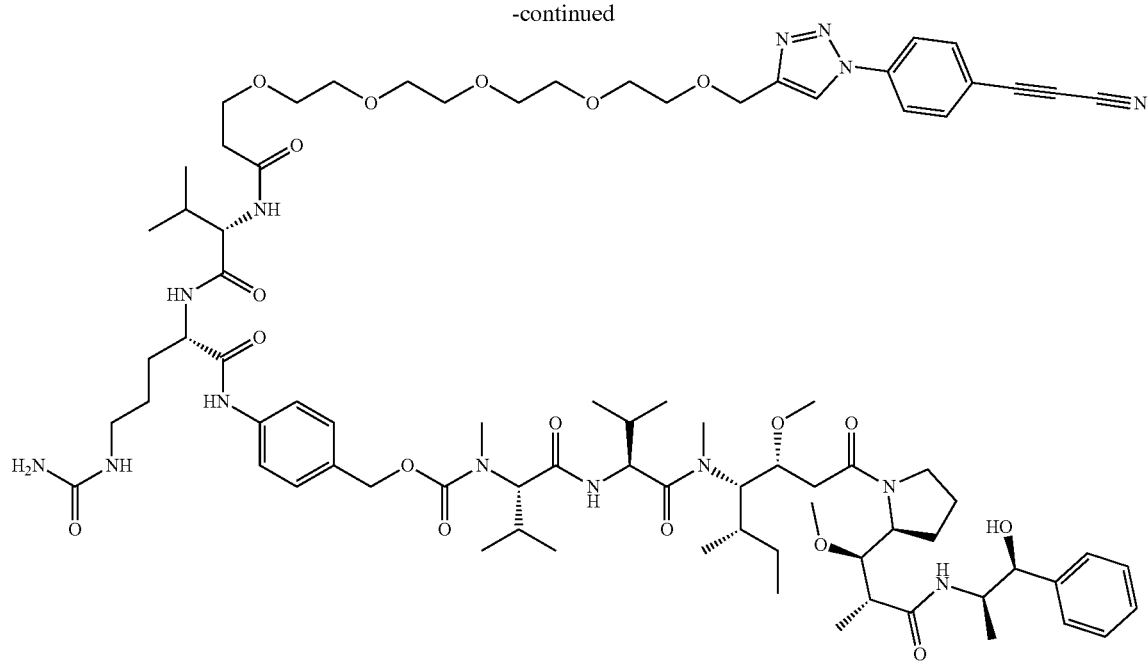

11

To the solution of 9 (1.2 eq., 35 mg, 74.1 μmol) in dry DMF (0.7 mL) was added 2-bromo-1-ethyl-pyridinium tetrafluoroborate (1.2 eq., 20.3 mg, 74.1 μmol). The resulting mixture was incubated at 21° C. for 5 min and then 10 (1 eq., 69.3 mg, 61.7 μmol) and N,N-diisopropylethylamine (5 eq., 39.9 mg, 53.8 μL, 308 μmol) were added. The resulting mixture was stirred at 21° C. for 30 min and the crude product was purified by preparative HPLC (Method A1) to yield compound 11 (49.7 mg, 31.5 μmol, 51%) as a white solid. MS (ESI) m/z: 789.2 [M+2H]$^{2+}$/2.

Compound 23

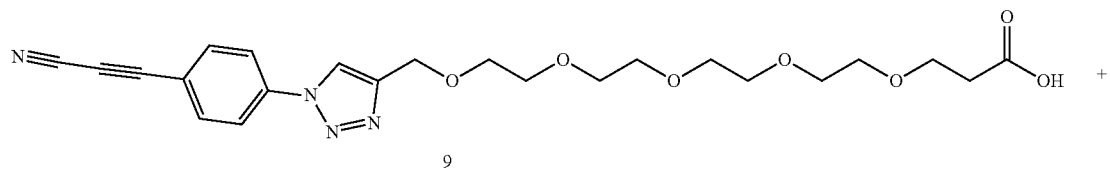

9

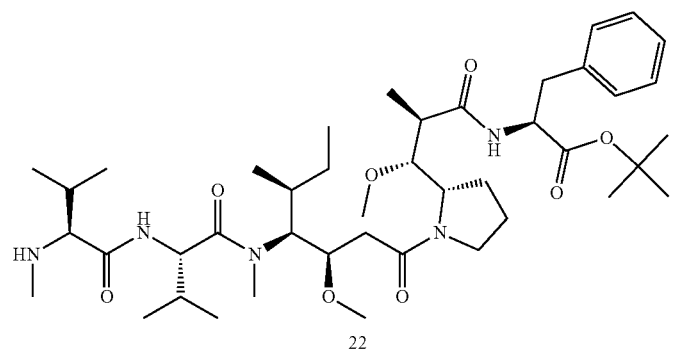

22

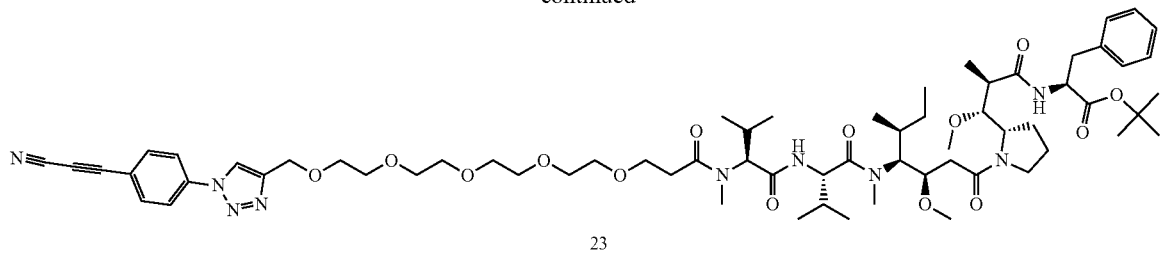

23

To the solution of 9 (1.2 eq., 75 mg, 158 μmol) in dry DMF (2 mL) was added 2-bromo-1-ethyl-pyridinium tetrafluoroborate (1.2 eq., 43.5 mg, 158 μmol). The resulting mixture was incubated at 21° C. for 5 minutes and then were added 22 (1 eq., 104 mg, 132 μmol) and DIEA (5 eq., 85.5 mg, 115 μL, 661 μmol). The resulting mixture was stirred at 21° C. for 3 hours and the crude mixture was purified by preparative HPLC (Method A1) to yield Compound 23 (18.1 mg, 14.6 μmol, 11%) as a white solid. MS (ESI) m/z: 621.7 $[M+2H]^{2+}/2$ Compound 24

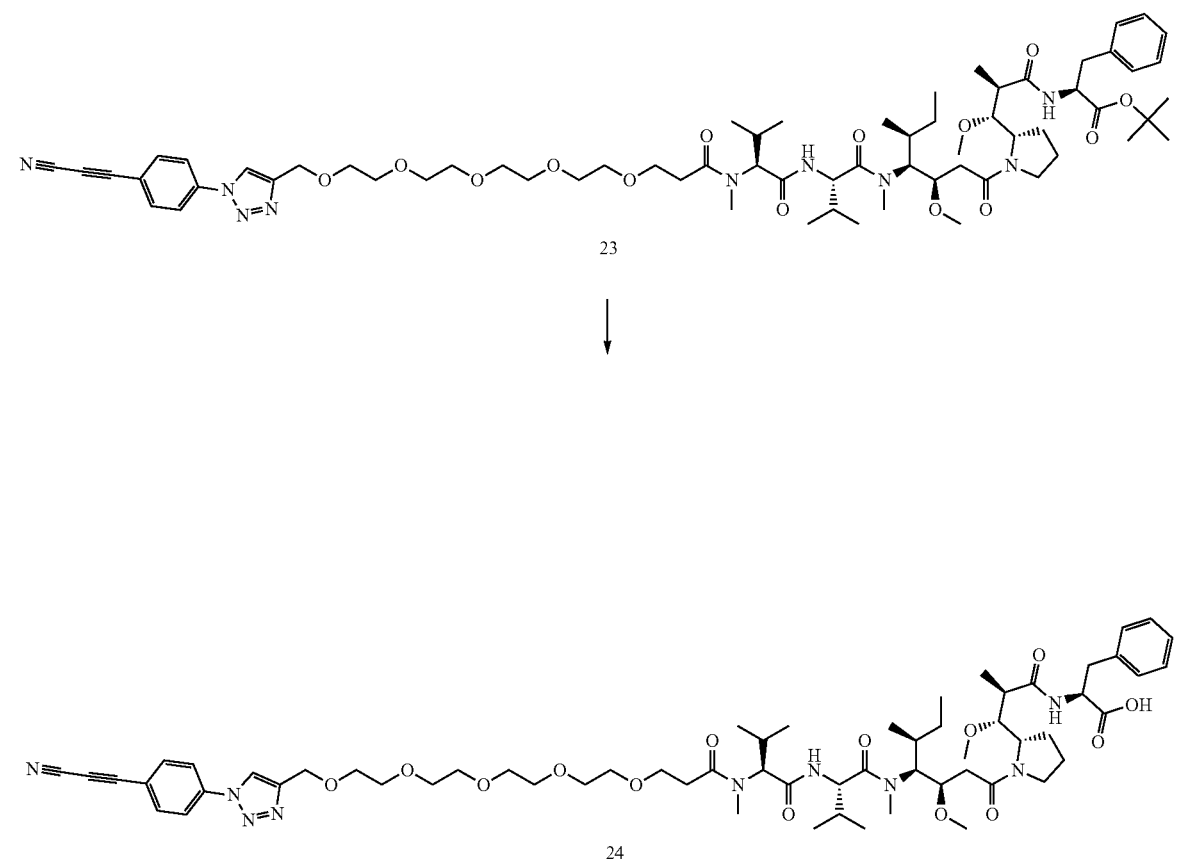

24

To the solution of 23 (1 eq., 18 mg, 14.5 μmol) in MeCN (1 mL) was added trifluoroacetic acid (0.1 mL, 1.346 mmol). The mixture was stirred at room temperature for 72 hours, concentrated and purified by preparative HPLC (Method A1) to yield Compound 24 (14.1 mg, 0.012 mmol, 82%) as a white solid.

MS (ESI) m/z: 604.8 $[M+H+Na]^{2+}/2$

Compound 34
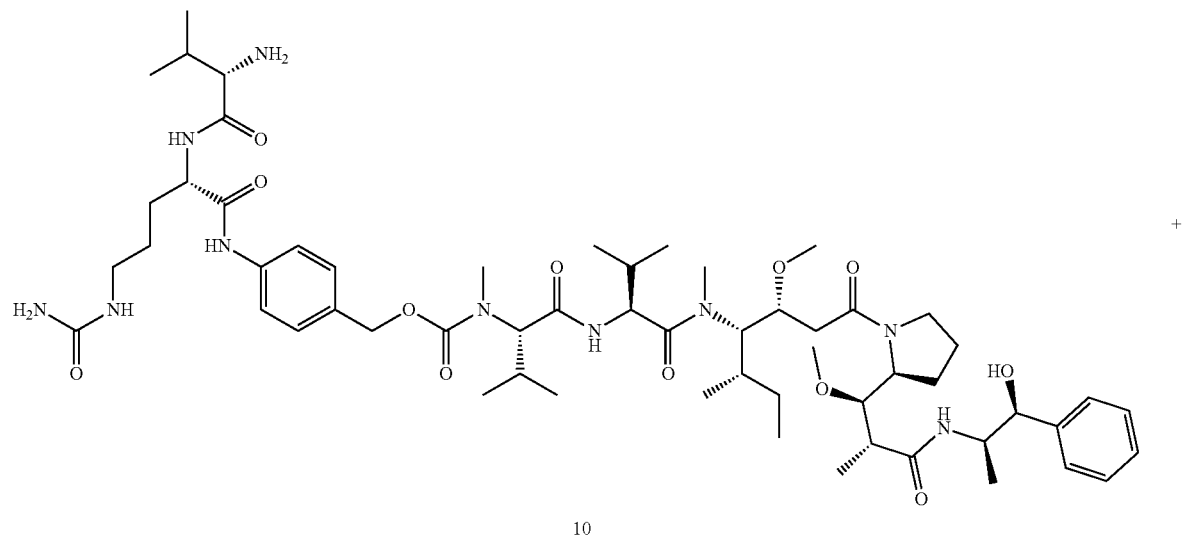
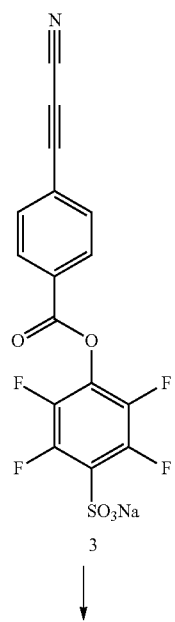

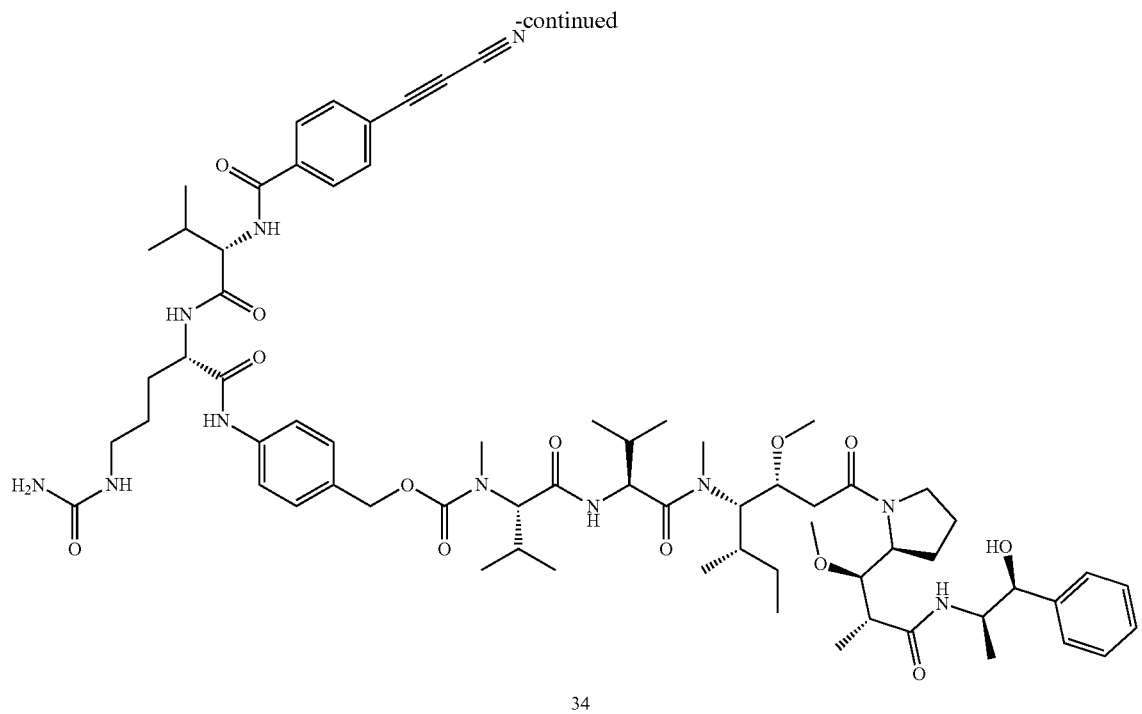

34

To the solution of 10 (1 eq., 30 mg, 0.0267 mmol) in dry DMF (1.5 mL) was added 3 (1.5 eq., 16.9 mg, 0.04 mmol) followed by DIEA (5 eq., 17.3 mg, 22.1 μL, 0.134 mmol) and the mixture was incubated at room temperature for 1 hour. The resulting mixture was purified by preparative HPLC (Method A1) to yield compound 34 (26.9 mg, 0.0211 mmol, 79%) as a white solid.

MS (ESI) m/z: 638.7 [M+2H]²/2

Example 2

Preparation of Protein-Drug Conjugates

General Procedure A for the Preparation of the Protein-Drug Conjugates.

To the solution of a Protein (5 mg/mL) in PBS (100 mM with 5 mM EDTA, pH 7.4) was added a solution of tris(2-carboxyethyl)phosphine hydrochloride (2 eq., 5 mM in H$_2$O). The mixture was incubated at 37° C. for 2 h. To the resulting solution was added a solution of a Payload (15 eq., 10 mM in DMSO). The mixture was incubated at 25° C. for 12 h and then centrifuged at 5000 g for 5 min. The supernatant was purified by size-exclusion chromatography (mobile phase: PBS 1×, stationary phase: Superdex 200) to yield pure Protein-Payload conjugate. In the structures of the conjugates described below m is an average number of Payloads attached per one Protein. In individual DAR (PPR) species m ranges from 0 to 8 (according to MS spectra and HIC chromatograms).

Compound 25 (T-APN-Gal-MMAE)

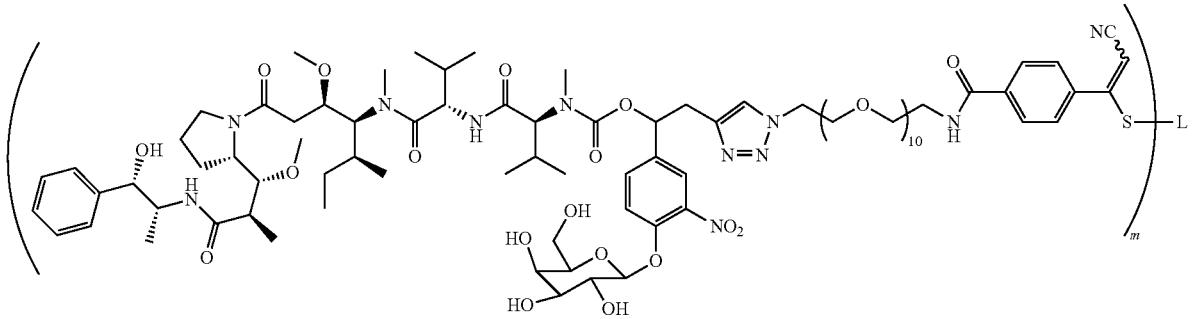

wherein L is Trastuzumab.

Compound 25 was prepared following General procedure A with Trastuzumab as a Protein and Compound 4 as a Payload.

Its PPR distribution is illustrated on FIG. 1.

Similar compounds may be prepared, in which L designates a cystein-containing protein residue.

Compound 26 (T-APN-Glu-MMAE)

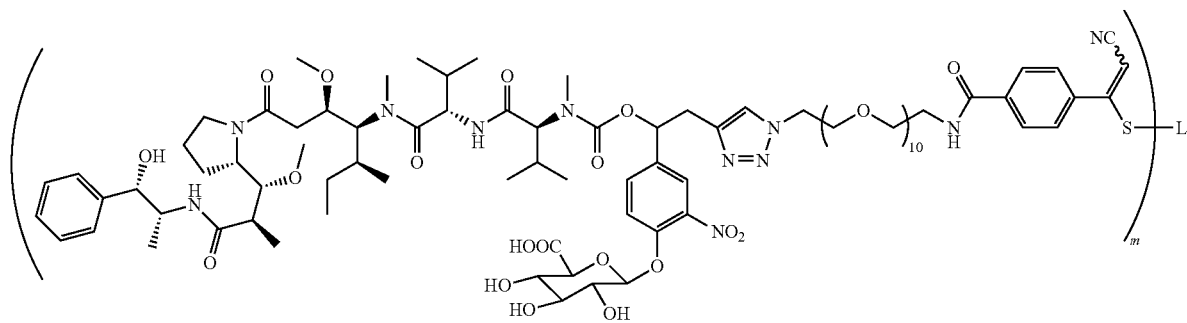

wherein L is Trastuzumab.

Compound 26 was prepared following General procedure A with Trastuzumab as a Protein and Compound 7 as a Payload.

Figure 2:
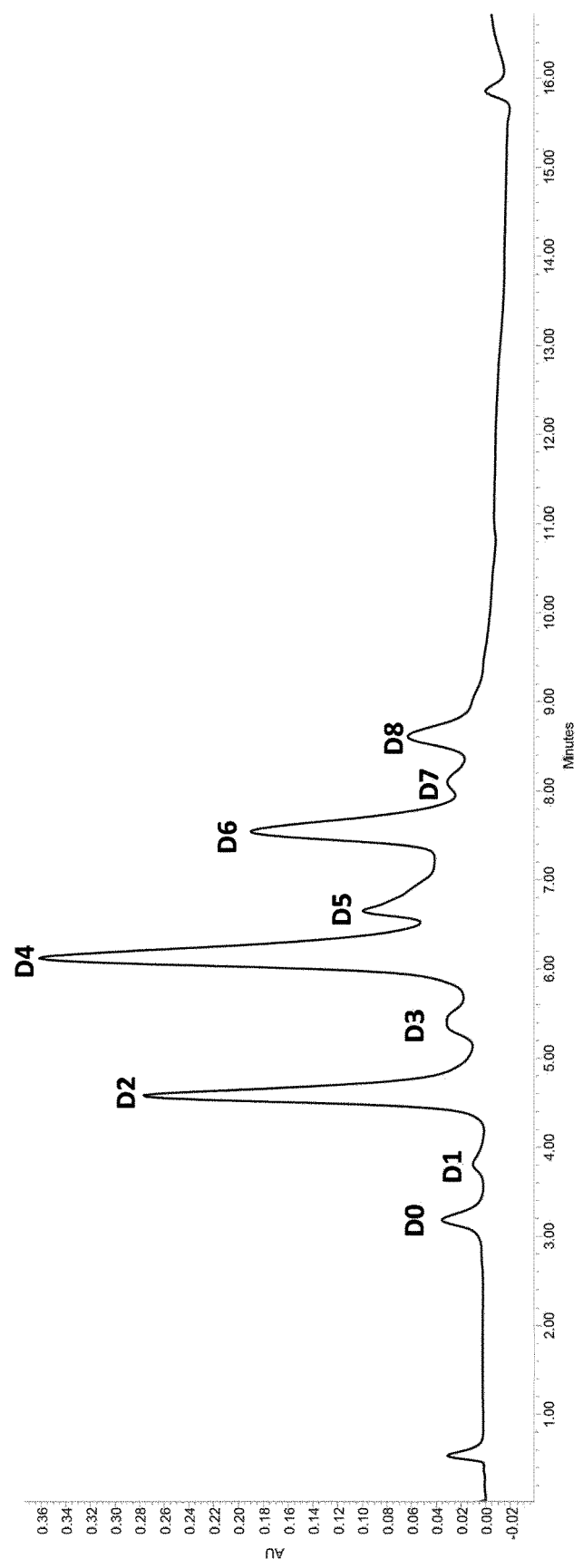
FIG. 2 illustrates the HIC chromatogram of Compound No. 26 prepared as described in Example 2.

Its PPR distribution is illustrated on FIG. 2.

Similar compounds may be prepared, in which L designates a cystein-containing protein residue.

Compound 27 (T-APN-PEG-VC-MMAE)

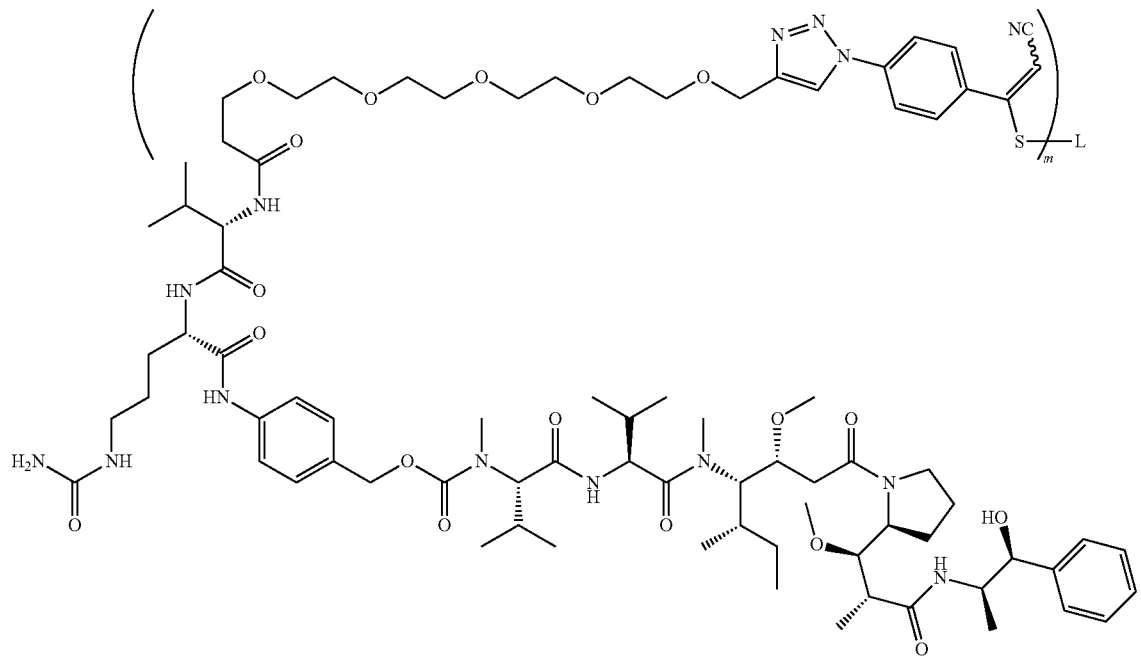

wherein L is Trastuzumab.

Compound 27 was prepared following General procedure A with Trastuzumab as a Protein and Compound 11 as a Payload.

Figure 3:
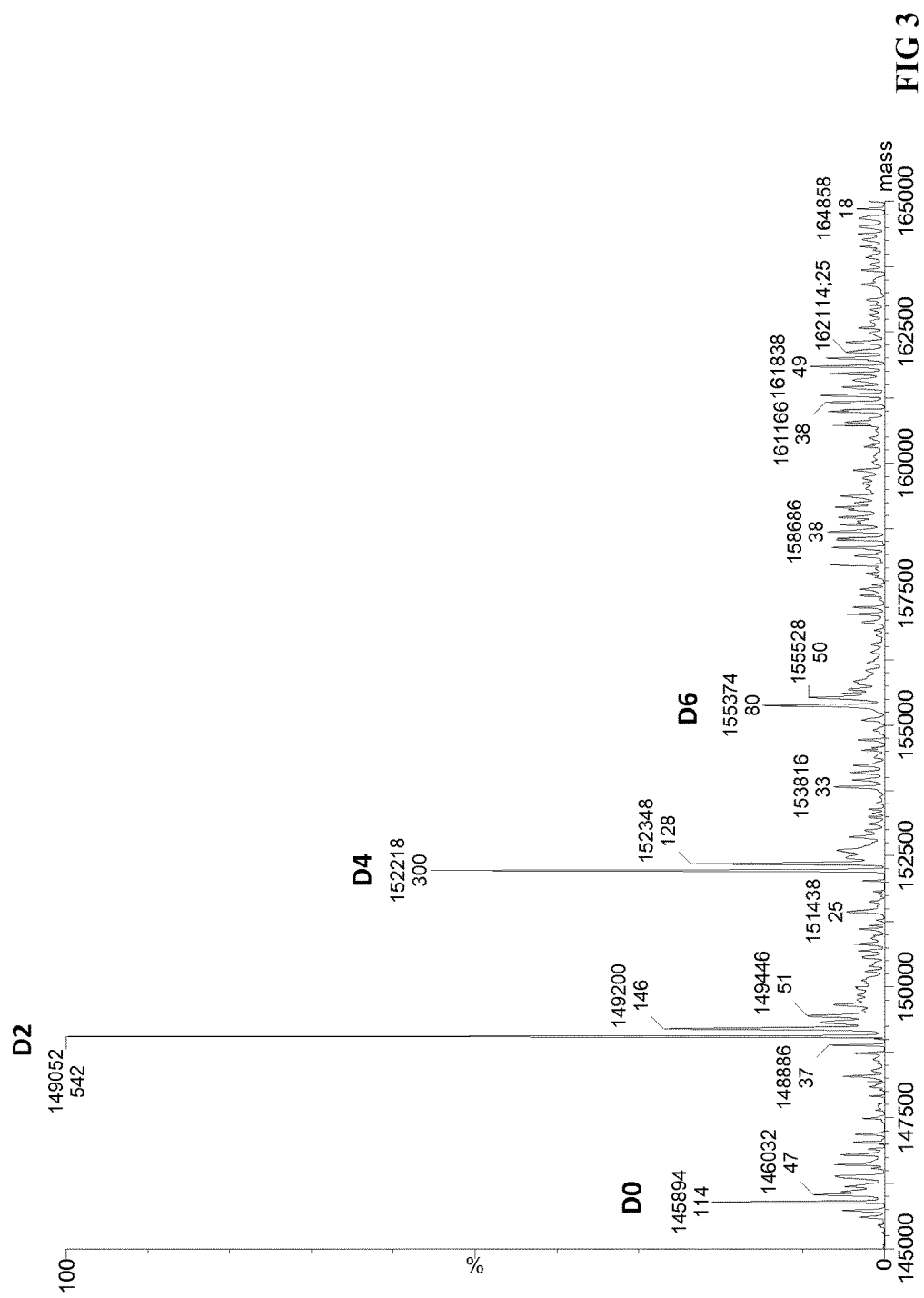
FIG. 3 shows the mass spectrum of deglycosylated Compound No. 27 prepared as described in Example 2.

Its PPR distribution is illustrated on FIG. 3.

Similar compounds may be prepared, in which L designates a cystein-containing protein residue.

Compound 31 (T-APN-MMAF)

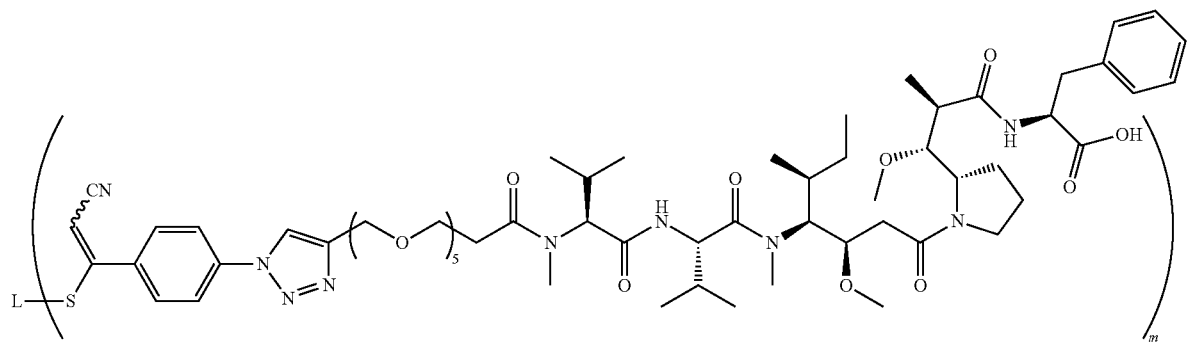

wherein L is Trastuzumab.

Compound 31 was prepared following General procedure A with Trastuzumab as a Protein and Compound 24 as a Payload.

Similar compounds may be prepared, in which L designates a cystein-containing protein residue.

Compound 32

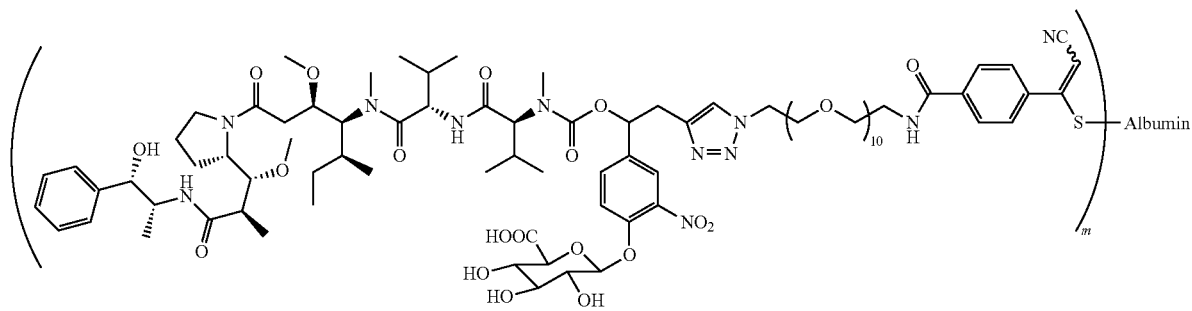

Figure 4:
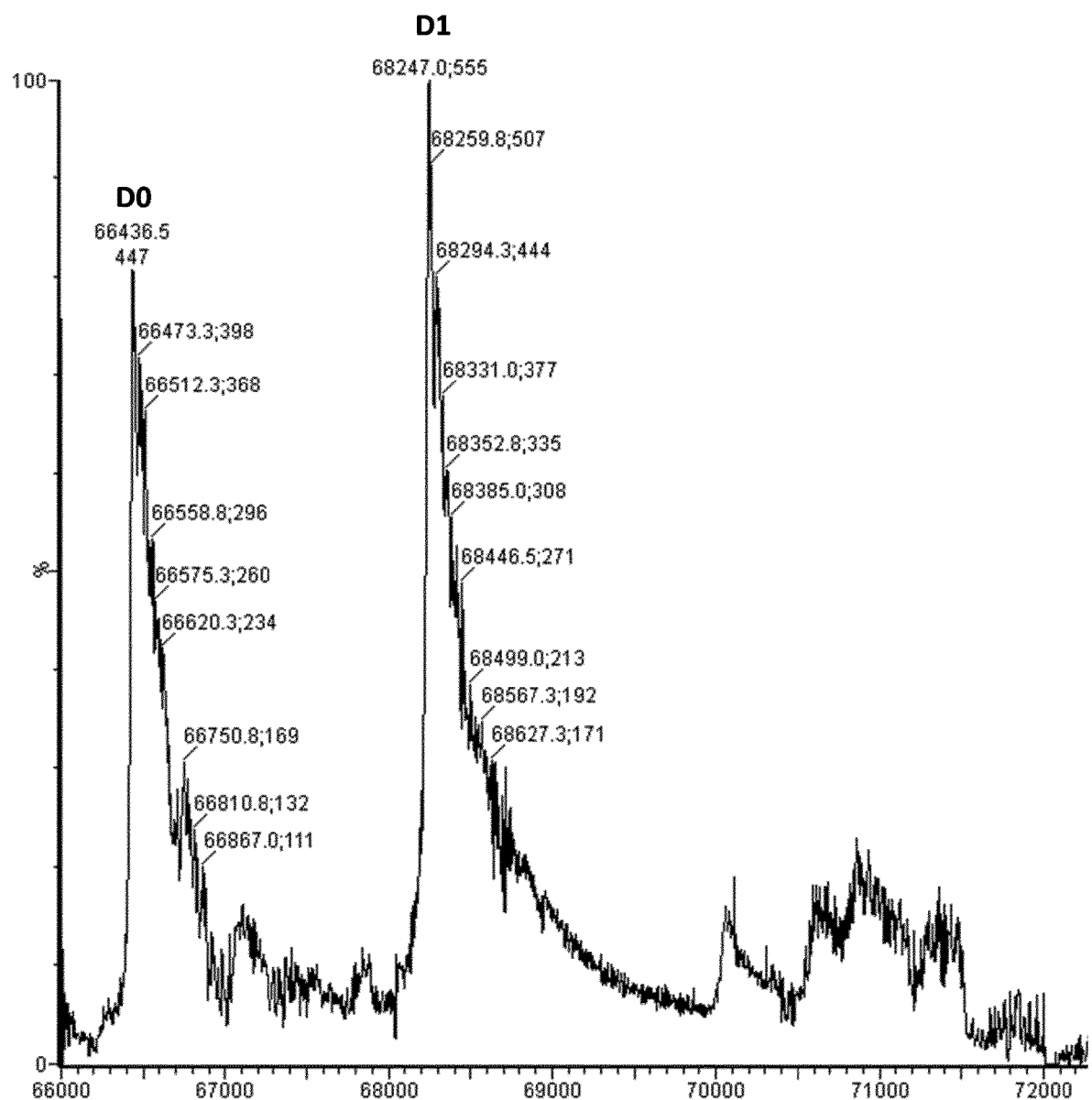
FIG. 4 shows the mass spectrum of Compound No. 32 prepared as described in Example 2.

To the solution of Albumin (5 mg/mL) in PBS (100 mM with 5 mM EDTA, pH 7.4) was added a solution of Compound 7 (15 eq., 10 mM in DMSO). The mixture was incubated at 25° C. for 12 h and then purified by size-exclusion chromatography (mobile phase: PBS 1×, stationary phase: Superdex 200) to yield pure Compound 32. Its PPR distribution is illustrated on FIG. 4.

Compound 33

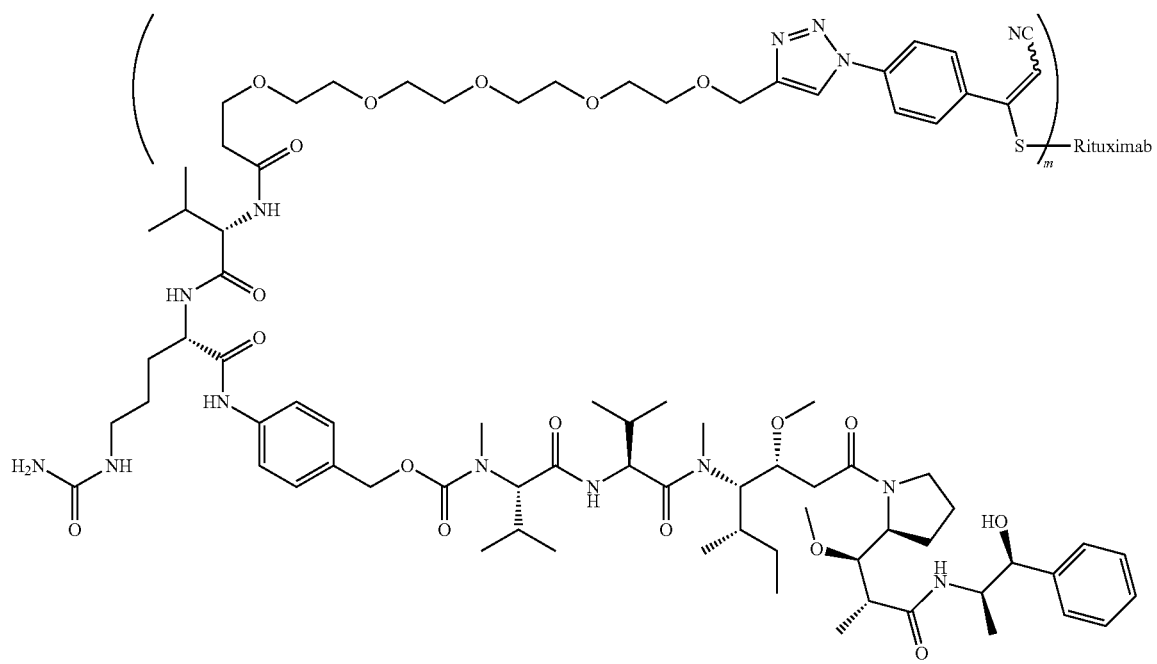

Compound 33 was prepared following General procedure A with Rituximab as a Protein and Compound 11 as a Payload.

Figure 5:
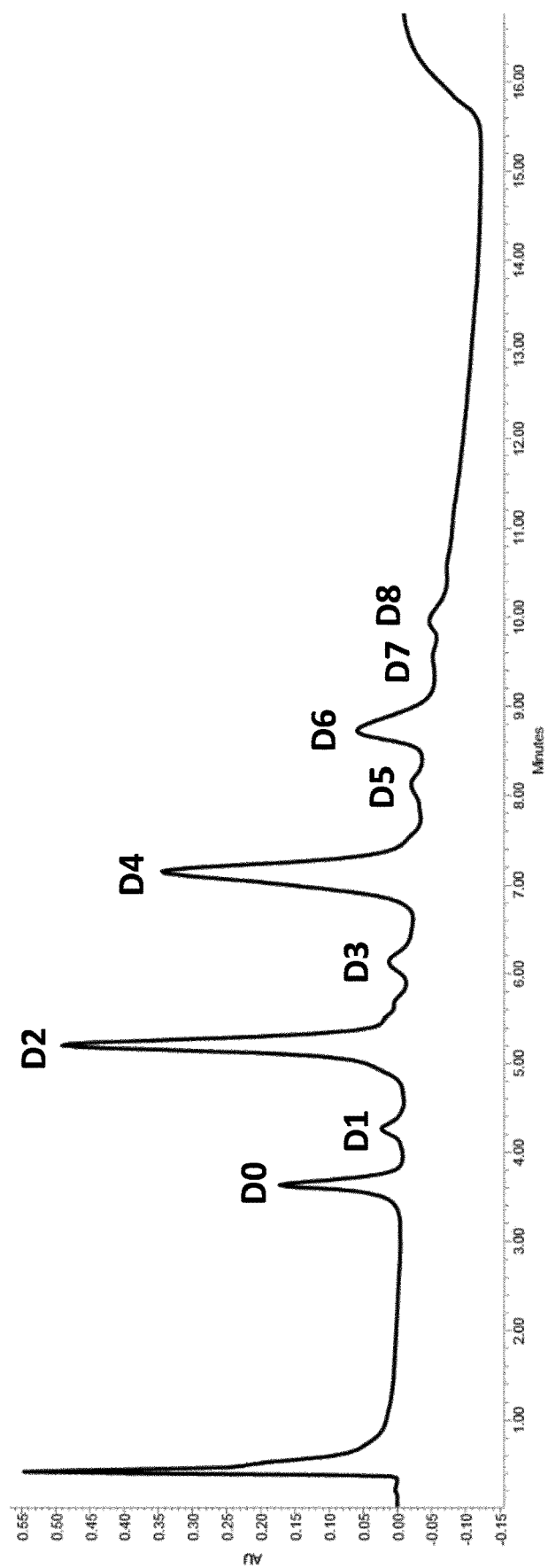
FIG. 5 illustrates the HIC chromatogram of Compound No. 33 prepared as described in Example 2.

Its PPR distribution is illustrated on FIG. 5.

Compound 35 (T-APN-VC-MMAE)

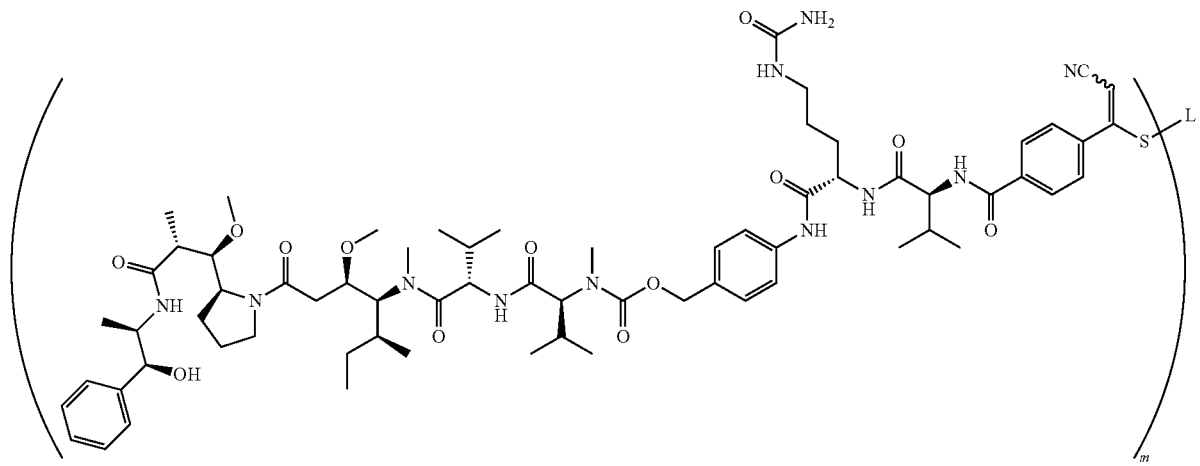

wherein L is Trastuzumab.

Compound 35 was prepared following General procedure A with Trastuzumab as a Protein and Compound 34 as a Payload.

Similar compounds may be prepared, in which L designates a cystein-containing protein residue.

Example 3

In Vitro Efficacy on Cell Viability

Antiproliferative activity of the ADCs according to this invention was evaluated on two cell lines and compared with that of the commercial ADC Kadcyla® (T-DM1).

Method

HER2+ SK-BR-3 and HER2− MDA-MB-231 cell lines were grown in DMEM—high glucose (4,500 mg/L) supplemented with 10% fetal calf serum, Penicillin (200 U/mL)-Streptomycin (200 µg/mL) and L-glutamin (4 mM) (all from Sigma Aldrich, St Louis, Mo., USA). The effects of the payloads and ADCs on these cell lines were assessed using CellTiter 96® AQueous One Solution Cell Proliferation Assay (Promega, Madison, Wis., USA). The cytotoxic agent MMAE was used as a positive control of cell death and every condition was performed as triplicates. SKBR-3 cells were plated in 96-well plates at 3,000 cells/well for ADC tests and at 5,000 cells/well for payload tests, in 100 µL medium. MDA-MB231 cells were plated in 96-well plates at 15,000 cells/well, in 100 µL medium. The cells were allowed to adhere for 24 hrs at 37° C. in a humidified atmosphere of 5% $CO_2$. Medium was then removed and replaced by payloads, ADCs, or MMAE, at different concentrations in fresh medium. A triplicate of cells on each plate was kept untreated as a negative control. After 96 hrs, the different treatments were replaced by fresh medium and CellTiter 96® AQueous One Solution (Promega) was used to determine the cell viability according to manufacturer's instructions. Absorbance was measured at 515 nm using a 96-well plate reader (Flx-Xenius XM, Safas, Monaco), and to estimate the percentage of viable cells according to each treatment, the negative controls were considered as 100% viability. GraphPad Prism 5 software was used to determine the $IC_{50}$ values for the different ADCs and MMAE.

Results

The results of these experiments are reported in the following table.

| Compound No. (ADC) | SK-BR-3 $IC_{50}$ (pM) | MDA-MB-231 $IC_{50}$ (pM) |
|---|---|---|
| 25 (T-APN-Gal-MMAE) | 14.3 | na* |
| T-DM1 | 33.0 | na* |

*no cytotoxic activity

| ADC | SK-BR-3 $IC_{50}$ (pM) | MDA-MB-231 $IC_{50}$ (pM) |
|---|---|---|
| 35 (T-APN-VC-MMAE) | 28.7 | na* |
| 27 (T-APN-PEG-VC-MMAE) | 19.6 | na* |
| T-DM1 | 34.2 | na* |

*no cytotoxic activity

As shown in this table, the ADCs of this invention dramatically affected the viability of HER2$^+$ SK-BR-3 cells, with $IC_{50}$ values in the picomolar range and were more potent than T-DM1. On the other hand, no cytotoxicity was observed on HER2$^-$ MDA-MB-231 cells until the highest tested dose. These results demonstrate the selective killing of HER2$^+$ cancer cells by the ADCs of this invention.

Example 4

In Vivo Anti-Tumour Efficacy

In vivo therapeutic efficacy of the ADCs of this invention was evaluated in nude mice bearing subcutaneous BT-474 tumors.

Method

Twenty (20) 6 to 8 week-old Balb/c nude (CByJ.Cg-Foxn1nu/J) females (Charles River Laboratories, L'Arbresles, France) were implanted with BT-474 ductal carcinoma cells ($2 \times 10^7$) suspended in 200 µL RPMI 1640 medium (Sigma Aldrich) containing matrigel (50:50, v:v, BD Biosciences, France). The injection was performed subcutaneously in the right flank. One day prior implant, the animals were gamma irradiated (2 Gy, $^{60}$Co). The cell transplant was considered as day 0 (D0). Once tumours reached a volume of 200-300 mm$^3$, mice were randomized according to their individual tumour volume into four distinct groups. The variance of mouse distribution within the groups was analysed to confirm the homogeneity of the groups. Groups and treatment protocols were as follow:

Groups 1—five (5) mice were i.v. injected with the vehicle (10 mM sodium succinate, pH 5);

Group 2—five (5) mice were i.v. injected with Compound No. 25 (T-APN-Gal-MMAE) (1 mg/kg, in sodium succinate, pH 5).

Group 3—five (5) mice were i.v. injected with T-DM1 (1 mg/kg in 10 mM sodium succinate, pH 5);

All animals had a single injection of either treatment or vehicle. Animal viability, behaviour and well-being were recorded daily; body weight was measured twice a week; and tumour volume was assessed twice a week with a calliper. The volume of the tumour was estimated formula as follow: volume=(width$^2 \times$length)/2.

Relative tumour volumes (RTV) were calculated according to the following formula:

$$RTV = \frac{\text{Mean tumor volume of ADC treated group at } Dx}{\text{Mean tumor volume of vehicle treated group at } Dx} \times 100$$

Results 31 days post-injection, the ADC of this invention induced a good anti-tumour response with 58% reduction of tumour volume, as compared to the control group. In the course of this experiment, the ADC was well tolerated without any loss in body weight or sign of over toxicity. On the other hand, the effect of T-DM1 on tumour growth was not statistically significant at the tested dose.

Nevertheless, the anticancer efficacy of T-DM1 was compared to that of the ADC of this invention using Principal Components Analysis (PCA).

Specifically, a principal component analysis (PCA) was carried out using XL Stat software (Addinsoft, Paris, France) in order to compare antitumour activity of T-DM1 and T-APN-Gal-MMAE.

PCA was based on mice tumour volumes throughout 45 days post-injection of a single 1 mg/kg intravenous dose of antibody-drug conjugate (n=5 mice per group). The two first principal dimensions (PCA 1 and 2) displayed a good inertia and described 92.9% of total variance. Mice were mainly discriminated along PCA 1 which explained 80.5% of information. This dimension was positively correlated with their tumour volumes, while the second axis was negatively correlated with the time course post-injection. On the individual plot, T-DM1 was opposed to T-APN-Gal-MMAE along PCA 1. This clearly stated in favour of a reduction of mice tumour volumes along the time with T-APN-Gal-MMAE.

The results of the PCA showed a higher reduction of tumour growth upon treatment with the ADC of this invention.

In addition, compared to ADCs similar to those of this invention but which do not comprise a cleavable unit and/or an arylpropiolonitrile moiety, the compounds of this invention provide improved efficacy (expressed by their IC50 for instance), plasmatic stability, release after internalisation on the tumour, therapeutic index and/or DAR homogeneity.

The invention claimed is:

1. Protein-drug conjugate having the following formula (I):

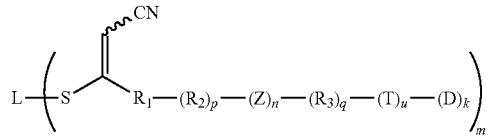 (I)

wherein:
L is a cysteine-containing protein residue linked through one or more of the cysteine groups of the protein,
$R_1$ is phenylene,
p and q are independently 0 or 1,
$R_2$ and $R_3$ are independently selected from the group consisting of —O—, —S—, —C(O)—, —NH—, —C(O)NH—, —NHC(O)—, —C(O)NR$_4$—, —NR$_4$C(O)—, wherein $R_4$ is a solubility unit selected from the group consisting of alkyl, where one or more H is or are substituted by any of the following fragments:

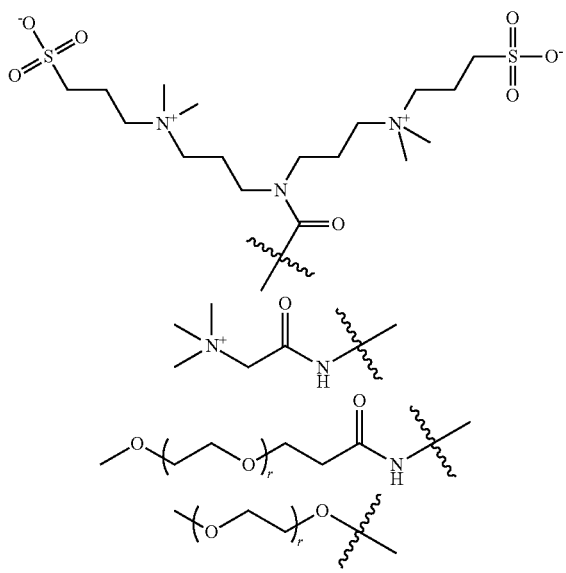

wherein r ranges from 1 to 24,
n is an integer from 0 to 5,
Z is a spacer selected from the group consisting of:
 a linear or branched, saturated or unsaturated, $C_1$-$C_{22}$ alkylene group optionally interrupted by one or more chemical groups selected from —O—, —S—, —C(O)—, —NH—, —C(O)NH—, —NHC(O)—, —C(O)NR$_4$— or —NR$_4$C(O)— wherein $R_4$ is as defined above,
 heteroarylene,
 a glycosyl group,
 an —O—(CH$_2$—CH$_2$—O—)$_t$ or —NH—(CH$_2$—CH$_2$—O—)$_t$ group in which t is an integer ranging from 1 to 24,
 an amino acid or peptide residue,
 wherein the spacers are identical to or different from each other when n is at least 2,
T is a cleavable unit sensitive to hydrolase, being the following group:

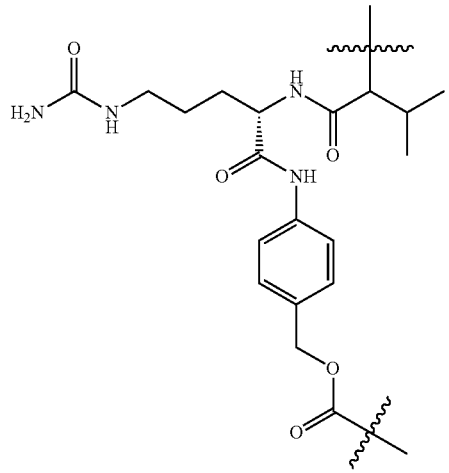 (T3)

u is 0 or 1,
k is 1 or 2,
each D is independently dolastatin,
m is the mean payload-to-protein ratio (PPR) of the conjugate, which ranges from 0.1 to 8,
wherein the cysteine-containing protein is a cysteine-containing antibody which binds specifically a protein present at the membrane of a cancer cell,
and wherein each dolastatin is independently linked to the T cleavable unit by a bond between the carbonyloxy function of the T cleavable unit and the nitrogen atom of the extremity of the dolastatin residue.

2. The protein-drug conjugate according to claim 1, wherein each dolastatin is independently selected from dolastatin 10, dolastatin 15, auristatin E, auristatin EB (AEB), auristatin EFP (AEFP), monomethyl auristatin F (MMAF), monomethyllauristatin-D (MMAD), monomethyl auristatin E (MMAE) and 5-benzoylvaleric acid-AE ester (AEVB).

3. The protein-drug conjugate according to claim 1, wherein the cysteine-containing protein is a monoclonal antibody.

4. The protein-drug conjugate according to claim 1, wherein the hydrolase is selected from a protease, Cathepsin B, a peptidase, an esterase, a glycosidase, a glucuronidase and a galactosidase.

5. The protein-drug conjugate according to claim 1, wherein Z is a spacer selected from the group consisting of:
 a linear or branched, saturated $C_1$-$C_{22}$ alkylene group optionally interrupted by one or more chemical groups selected from —O— and —C(O)NH—,
 a heteroarylene group.

6. The protein-drug conjugate according to claim 1, wherein:
p is 0 or 1 and $R_2$ is —CONH—,
n is an integer from 0 to 2,
q is 0 or 1 and $R_3$ is selected from the group consisting of —C(O)— and —CONH—
u is 1.

7. The protein-drug conjugate according to claim 1, wherein:
p is 0,
n is 1,
q is 1 and $R_3$ is —C(O)NH—, and
u is 1.

8. The protein-drug conjugate according to claim 1, which has any of the following structures:
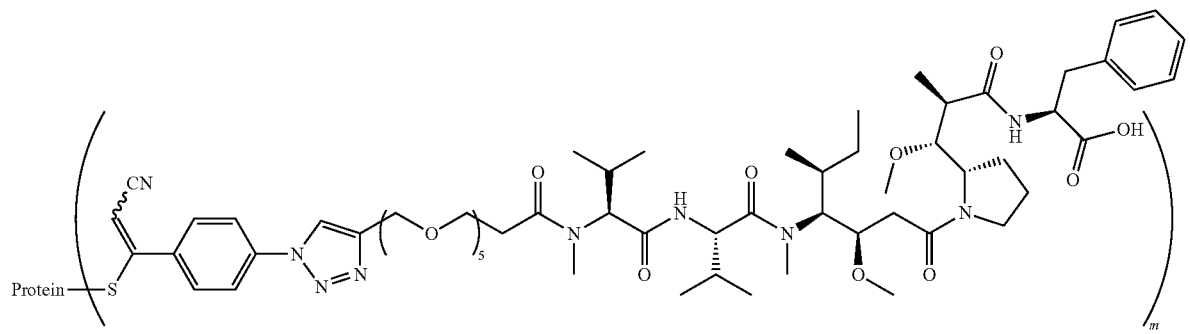
wherein "Protein" designates a cysteine-containing protein residue
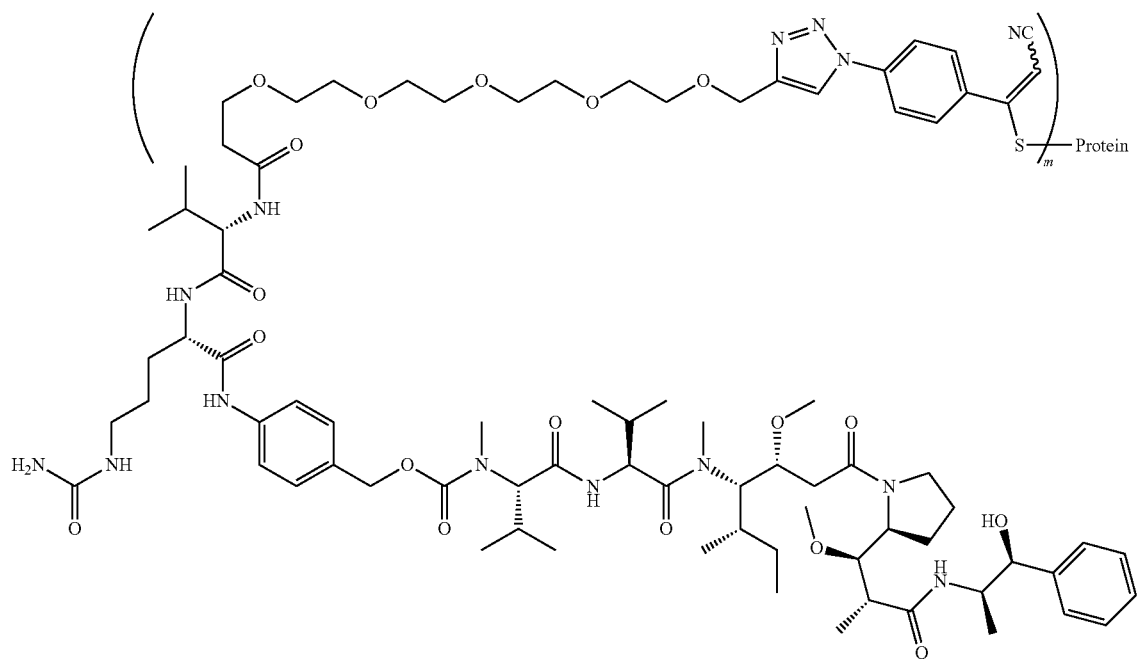
wherein "Protein" designates a cysteine-containing protein residue

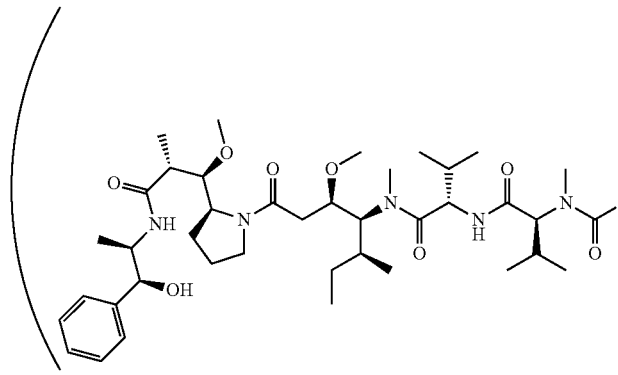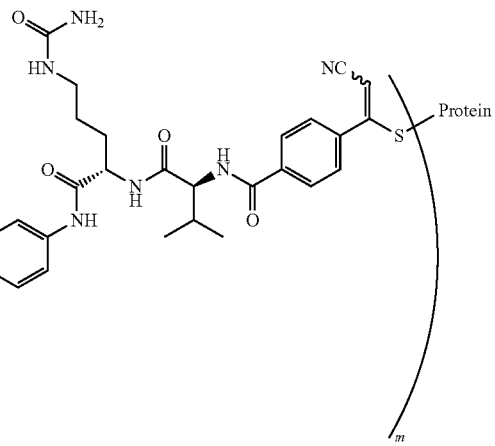

wherein "Protein" designates a cysteine-containing protein residue wherein, in the above formulas, m is the mean Payload-to-Protein Ratio of the conjugate which ranges from 0.1 to 8, wherein the cysteine-containing protein is a cysteine-containing antibody which binds specifically a protein present at the membrane of a cancer cell.

9. A pharmaceutical composition comprising an effective amount of at least one of the protein-drug conjugates according to claim 1 and a pharmaceutically acceptable carrier.

10. A method for treating a cancer in a subject, comprising administering to the subject suffering from a cancer a therapeutically effective amount of the protein-drug conjugate according to claim 1.

11. A method for treating a cancer in a subject, comprising administering to the subject suffering from a cancer a therapeutically effective amount of the pharmaceutical composition according to claim 9.

12. The protein-drug conjugate according to claim 1, wherein n is from 0 to 2.

13. The protein-drug conjugate according to claim 1, wherein the hydrolase is an intracellular hydrolase.

14. The protein-drug conjugate according to claim 8, wherein the cysteine-containing antibody is IgG.

15. The protein-drug conjugate according to claim 8, wherein the cysteine-containing antibody is IgG1 or IgG4.

16. The protein-drug conjugate according to claim 1, wherein the cytotoxic drug is selected from MMAE, MMAF and MMAD.

17. The protein-drug conjugate according to claim 1, wherein the cytotoxic drug is MMAE.

\* \* \* \* \*